United States Patent
Chen et al.

(10) Patent No.: US 9,238,654 B2
(45) Date of Patent: Jan. 19, 2016

(54) SINGLETON INHIBITORS OF SUMOYLATION ENZYMES AND METHODS FOR THEIR USE

(71) Applicants: CITY OF HOPE, Duarte, CA (US); Sanford-Burnham Medical Research Institute at Lake Nona, Orlando, FL (US)

(72) Inventors: Yuan Chen, Arcadia, CA (US); Yi-Jia Li, Duarte, CA (US); Daniela Divlianska, Orlando, FL (US); Ekaterina Bobkova, Orlando, FL (US); Greg Roth, Orlando, FL (US)

(73) Assignees: City of Hope, Duarte, CA (US); Sanford-Burnham Medical Research Institute at Lake Nona, Orlando, FL (US)

( * ) Notice: Subject to any disclaimer, the term of this patent is extended or adjusted under 35 U.S.C. 154(b) by 313 days.

(21) Appl. No.: 13/891,067

(22) Filed: May 9, 2013

(65) Prior Publication Data
US 2013/0317101 A1 Nov. 28, 2013

Related U.S. Application Data

(63) Continuation of application No. PCT/US2011/060064, filed on Nov. 9, 2011.

(60) Provisional application No. 61/411,855, filed on Nov. 9, 2010.

(51) Int. Cl.
| | | |
|---|---|---|
| *A61K 31/34* | (2006.01) | |
| *C07D 493/08* | (2006.01) | |
| *C07D 487/04* | (2006.01) | |
| *A61K 31/555* | (2006.01) | |
| *A61K 33/24* | (2006.01) | |
| *A61K 41/00* | (2006.01) | |
| *A61K 45/06* | (2006.01) | |

(52) U.S. Cl.
CPC .............. *C07D 487/04* (2013.01); *A61K 31/34* (2013.01); *A61K 31/555* (2013.01); *A61K 33/24* (2013.01); *A61K 41/00* (2013.01); *A61K 45/06* (2013.01); *C07D 493/08* (2013.01)

(58) Field of Classification Search
CPC ............................. A61K 31/34; C07D 493/08
USPC ............................ 514/469; 435/184; 549/463
See application file for complete search history.

(56) References Cited

U.S. PATENT DOCUMENTS

| | | | |
|---|---|---|---|
| 7,893,016 B2 * | 2/2011 | Pathirana et al. | 514/1.1 |
| 8,283,113 B2 * | 10/2012 | Dmitrovsky et al. | 435/4 |
| 2002/0127692 A1 * | 9/2002 | Ink et al. | 435/226 |
| 2004/0053388 A1 * | 3/2004 | Eckert et al. | 435/194 |
| 2005/0158808 A1 * | 7/2005 | Kikuchi et al. | 435/7.23 |

* cited by examiner

*Primary Examiner* — Raymond Henley, III
(74) *Attorney, Agent, or Firm* — Mintz, Levin, Cohn, Ferris, Glovsky and Popeo, P.C.

(57) ABSTRACT

According to the embodiments described herein, a SUMOylation inhibitor compound comprising a singleton scaffold is provided. In some embodiments, a method for inhibiting a SUMOylation enzyme in a cell is provided. Such a method may include administering a SUMOylation inhibitor compound to the cell. In some aspects, the SUMOylation enzyme is SUMO E1 or SUMO E2. In some aspects, the method may be used to inhibit a cancer cell in vitro (e.g., grown in culture) or in vivo (e.g., as part of a tumor in a subject). In other embodiments, a method for treating a cancer, degenerative diseases and viral infection is provided. Such a method may include administering an effective amount of a pharmaceutical composition to a subject having the cancer. The pharmaceutical composition may include a singleton SUMOylation inhibitor compound. In some embodiments, the method for treating a cancer may further comprise administering one or more DNA-damaging therapy in combination with administration of the pharmaceutical composition.

19 Claims, 15 Drawing Sheets

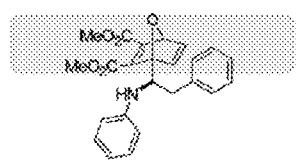

MLS-0437113
SUMOylation:
IC$_{50}$(-BSA) 0.33±0.02 uM (n=3)
IC$_{50}$(+BSA) 0.47±0.07 uM (n=8)
Ubc13: inactive 37 analogs made Mono ester hydrolysis leads to a 10x drop in potency.

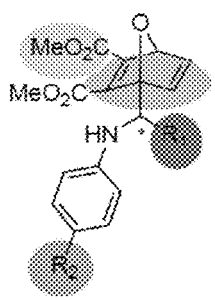

$R_2$ = H, Cl, Me, OMe
15x decrease in potency

Double bond reduction renders the molecule inactive.

$R_1$ = Aromatic:
   CH$_2$Ph, CH$_2$C$_6$H$_4$Me,
   CH$_2$C$_6$H$_4$OMe, CH$_2$C$_6$H$_4$F
No significant change w/i the series $R_1$ = Aliphatic:
   n-Pr, Allyl, Vinyl, Me
15x decrease in activity

Figure 3

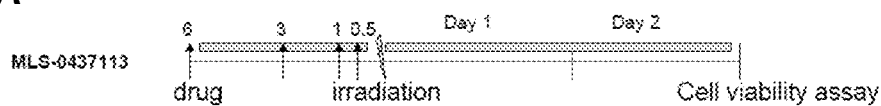
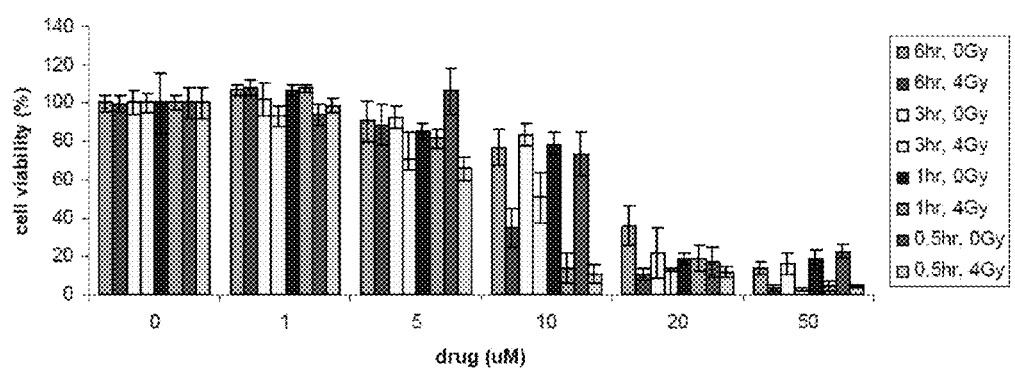
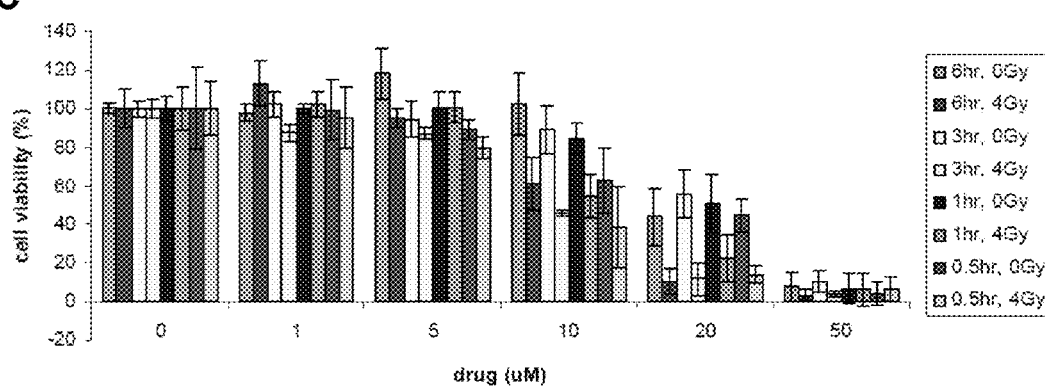
Figure 11

Figure 13

| # | CPCCG MLS- | ^ | R1 | R2 | * | n | SUMO -/+ BSA | n | Ubc13 | Sel. | Purity, %[a] |
|---|---|---|---|---|---|---|---|---|---|---|---|
| 1 | 0437113 | S | benzyl | H | R | 3 | 0.33±0.02 | 3 | >100 | >303 | >95 |
|   |   |   |   |   |   | 8 | 0.47±0.07 |   |   | >213 |   |
| 2 | 0437317 | S | 4-substituted benzyl | H | R | 4 | 0.37±0.03 | 3 | >100 | >270 | >95 |
|   |   |   |   |   |   | 3 | 0.47±0.05 |   |   | >213 |   |
| 3 | 0437320 | S | 4-F benzyl | H | R | 3 | 0.53±0.14 | 3 | >100 | >189 | 90 (55:45dr) |
|   |   |   |   |   |   | 3 | 1.1±0.15 |   |   | >91 |   |
| 4 | 0437319 | S | 4-OMe benzyl | H | R | 4 | 0.61±0.07 | 3 | >100 | >164 | >95 |
|   |   |   |   |   |   | 3 | 0.68±0.06 |   |   | >147 |   |
| 5 | 0437321 | S | 4-OCF3 benzyl | H | R | 6 | 0.61±0.08 | 3 | 84±27 | 138 | 90 (52:48dr) |
|   |   |   |   |   |   | 3 | 0.80±0.16 |   |   | 125 |   |
| 6 | 0437313 | S | iPr | H | R | 4 | 0.53±0.08 | 3 | >100 | >189 | >95 |
|   |   |   |   |   |   | 3 | 0.48±0.06 |   |   | >208 |   |
| 7 | 0437111 | S |   |   |   | 3 | 1.8±0.79 | 3 | >100 | >56 | >95 |
|   |   |   |   |   |   | 3 | 3.3±0.58 |   |   | >30 |   |
| 8 | 0084028 | P1 | allyl | H | R |   |   | 3 | >100 |   | >95[b] (83:17dr) |
|   |   |   |   |   |   | 3 | 3.3±? |   |   | >30 |   |
| 9 | 0084028 | P2 |   |   |   | 3 | 1.4±0.34 | 3 | >100 | >71 | >95 (83:17dr) |
|   |   |   |   |   |   | 3 | 3.8±0.02 |   |   | >26 |   |
| 10 | 0437315 | S | vinyl | H | R | 3 | 7.2±1.0 | 3 | >100 | >14 | >95 |
|   |   |   |   |   |   | 3 | 7.2±0.49 |   |   | >14 |   |
| 11 | 0437104 | S | Et | H | R | 3 | 7.8±1.7 | 3 | >100 | >13 | >95 |
|   |   |   |   |   |   | 3 | 12±3.7 |   |   | >8.3 |   |
| 12 | 0437322 | S | structure |   | R | 3 | 2.9±0.24 | 3 | >100 | >34 | >95 |
|   |   |   |   |   |   | 3 | 5.2±0.60 |   |   | >19 |   |
| 13 | 0437279 | S | structure |   | R | 3 | >100 | 3 | >100 | - | >95 |
|   |   |   |   |   |   | 3 | >100 |   |   | - |   |

Figure 13 (Cont'd)
| SAR Analysis for SUMOylation (Medicinal Chemistry) | | | | | | Potency (uM) mean ± S.E.M. (n = replicates) | | | | Purity, %[a] |
|---|---|---|---|---|---|---|---|---|---|---|
| # | CPCCG MLS- | ^ | R1 | R2 | * | n | SUMO -/+ BSA | n | Ubc13 | Sel. | |
| 14 | 0437120 | S | 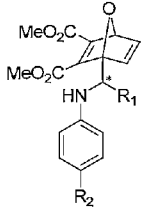 benzyl | Cl | R | 3 | 0.71±0.07 | 3 | >100 | >141 | >95 |
|  |  |  |  |  |  | 3 | 5.2±0.41 |  |  | >19 |  |
| 15 | 0437109 | S | 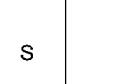 benzyl | Me | R | 3 | 3.0±0.07 | 3 | >100 | >33 | >95 |
|  |  |  |  |  |  | 3 | 6.9±1.0 |  |  | >14 |  |
| 16 | 0437118 | S | 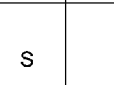 benzyl | OMe | R | 3 | 4.9±1.0 | 3 | >100 | >20 | >95 |
|  |  |  |  |  |  | 3 | 9.5±2.5 |  |  | >11 |  |
| 17 | 0437126 | S | 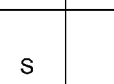 allyl | Cl | R | 3 | 3.8±0.44 | 3 | >100 | >26 | >95 |
|  |  |  |  |  |  | 3 | 13±2.7 |  |  | >7.7 |  |
| 18 | 0437116 | S |  allyl | Me | R | 3 | 12±1.2 | 3 | >100 | >8.3 | >95 |
|  |  |  |  |  |  | 3 | 16±8.3 |  |  | >6.3 |  |
| 19 | 0437123 | S | 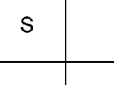 allyl | OMe | R | 3 | 22±3.5 | 3 | 93±12 | 4.2 | >95 |
|  |  |  |  |  |  | 3 | 24±9.0 |  |  | 3.9 |  |
| 20 | 0437128 | S | 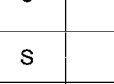 Me | Cl | R | 3 | 18±0.59 | 3 | >100 | >5.6 | >95 |
|  |  |  |  |  |  | 3 | 25±7.1 |  |  | >4.0 |  |
| 21 | 0437122 | S | 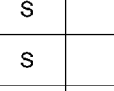 Me | Me | R | 3 | 35±6.1 | 3 | >100 | >2.9 | >95 |
|  |  |  |  |  |  | 3 | 35±11 |  |  | >2.9 |  |
| 22 | 0437125 | S | 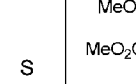 Me | OMe | R | 3 | 56±8.1 | 3 | >100 | >1.8 | >95 |
|  |  |  |  |  |  | 3 | 45±12 |  |  | >2.2 |  |
| 23 | 0437107 | S |  | | R | 3 | 21.3 | 3 | >100 | >4.7 | >95 |
|  |  |  |  |  |  | 3 | 29.9 |  |  | >3.3 |  |

Figure 13 (Cont'd)

| SAR Analysis for SUMOylation (Medicinal Chemistry) | | | (structure) | | | Potency (uM) mean ± S.E.M. (n = replicates) | | | | Purity, %[a] |
|---|---|---|---|---|---|---|---|---|---|---|
| # | CPCCG MLS- | ^ | R1 | R2 | * | n | SUMO -/+ BSA | n | Ubc13 | Sel. | |
| 24 | 0437314 | S | (iPr) | H | S | 3 | 2.9±0.15 | 3 | >100 | >34 | >95 (88:12dr) |
|    |         |   |      |   |   | 3 | 3.2±0.48 |   |      | >31 |              |
| 26 | 0437318 | S | (p-tolyl-CH2) | H | S | 3 | 2.2±0.58 | 3 | >100 | >45 | >95 (93:7dr) |
|    |         |   |              |   |   | 3 | 3.8±0.37 |   |      | >26 |              |
| 27 | 0437114 | S | (Bn) | H | S | 3 | 5.0±1.6 | 3 | >100 | >20 | 90 (80:20dr) |
|    |         |   |      |   |   | 3 | 12±1.8  |   |      | >8.3 |              |
| 25 | 0437112 | S | (allyl) | H | S | 3 | 6.0±1.7 | 3 | >100 | >17 | 90 (80:20dr) |
|    |         |   |         |   |   | 3 | 15±2.8  |   |      | >6.7 |              |
| 28 | 0437316 | S | (iBu) | H | S | 3 | 10±0.56 | 3 | 52 | 5.2 | >95 |
|    |         |   |       |   |   | 3 | 11±0.70 |   |    | 4.7 |     |
| 29 | 0437105 | S | (Me) | H | S | 3 | 24±4.0 | 3 | 80 | 3.3 | >95 |
|    |         |   |      |   |   | 3 | 25±6.9 |   |    | 3.2 |     |
| 30 | 0437121 | S | (Bn) | Cl | S | 3 | 2.6±1.1 | 3 | >100 | >38 | >95 |
|    |         |   |      |    |   | 3 | 9.2±2.4 |   |      | >11 |     |
| 31 | 0437127 | S | (allyl) | Cl | S | 3 | 4.2±0.58 | 3 | >100 | >24 | >95 |
|    |         |   |         |    |   | 3 | 12±1.0   |   |      | >8.3 |     |
| 32 | 0437129 | S | (Me) | Cl | S | 3 | 12±2.6 | 3 | 53 | 4.4 | >95 |
|    |         |   |      |    |   | 3 | 17±4.8 |   |    | 3.1 |     |
| 33 | 0437110 | S | (Bn) | Me | S | 3 | 7.2±0.58 | 3 | >100 | >14 | >95 |
|    |         |   |      |    |   | 3 | 11±2.8   |   |      | >9.1 |     |
| 34 | 0437117 | S | (allyl) | Me | S | 3 | 12±0.54 | 3 | >100 | >8.3 | >95 |
|    |         |   |         |    |   | 3 | 17±2.9  |   |      | >3.1 |     |
| 35 | 0437119 | S | (Bn) | OMe | S | 3 | 13±3.1 | 3 | >100 | >7.7 | >95 |
|    |         |   |      |     |   | 3 | 13±4.8 |   |      | >7.7 |     |
| 36 | 0437124 | S | (allyl) | OMe | S | 3 | 18±2.8 | 3 | >100 | >5.6 | >95 |
|    |         |   |         |     |   | 3 | 23±7.7 |   |      | >4.3 |     |
| 37 | 0437108 | S | (structure) |  | S | 3 | 15.1 | 3 | >100 | >6.6 | >95 |
|    |         |   |             |  |   | 3 | 18.4 |   |      | >5.4 |     |

SINGLETON INHIBITORS OF SUMOYLATION ENZYMES AND METHODS FOR THEIR USE

RELATED APPLICATIONS

This application is a continuation application of PCT Application No. PCT/US2011/60064, filed Nov. 9, 2011, which claims the benefit of U.S. Provisional Application No. 61/411,855, filed Nov. 9, 2010, which are hereby incorporated in their entirety and for all purposes.

GOVERNMENT INTEREST

The invention was made with Government support under Grant Nos. R01 GM086172, F32 CA134180, and R03 DA026556-01 awarded by the National Institutes of Health (NIH). The Government has certain rights in the invention.

BACKGROUND

Post-translational modifications of cellular proteins by the small ubiquitin-like modifier (SUMO) family of proteins are important epigenetic mechanisms for regulating various cellular functions. At least three members of the SUMO family (SUMO-1, -2, and -3) are ubiquitin-like proteins that can conjugate to other cellular proteins by a biochemical mechanism similar to ubiquitination (Hay 2005; Sarge 2009; Yeh 2009).

SUMOylation requires multiple steps that are catalyzed by three types of SUMOylation enzymes: activating enzyme E1 (made up of two subunits, SAE1 and SAE2/Uba2), conjugating enzyme E2 (Ubc9), and one of approximately ten E3 ligases. This pathway is illustrated for SUMO 1 in FIG. 1. Briefly, SUMO is activated by the E1 enzyme through ATP hydrolysis and forms a thioester conjugate with E1. SUMO is then transferred to E2, forming a thioester conjugate with E2. Finally, SUMO is transferred to target proteins, a step usually stimulated by an E3 ligase. SUMO modification adds a new docking site to target proteins, and thus enables new protein-protein interactions through the SUMO-interacting motif (SIM) in receptor proteins (Song 2004; Song 2005). The E1 and E2 enzymes do not discriminate among the different SUMO paralogues (Tatham 2003).

SUMOylation is reversible by a process known as deSUMOlyation. The removal of SUMO proteins from modified target proteins is accomplished by deSUMOylation enzymes such as isopeptidase and SUMO/sentrin-specific protease (SENP).

Aberrations in post-translational modification of cellular proteins by the small ubiquitin-like modifier (SUMO) family of proteins are associated with the pathogenesis of life-threatening diseases, such as cancer (Luo 2009; Kim 2006; Mo 2005), neurodegenerative disorders (Steffan 2004; Subramaniam 2009), and viral infection (Jaber 2009; Ulrich 2009; Kim 2010). Viral infection often involves hijacking the host post-translational modifications, providing viruses with a fast means for becoming established in host cells before the immune system can respond.

SUMOylation and deSUMOylation enzymes regulate dynamic SUMO modifications in controlling cellular functions. One of the predominant functions of SUMO-mediated modifications is in DNA damage response, such as damage caused by chemo- and radiation therapy (CRT), which kills cancer cells by inducing genotoxic stress (Galanty 2009; Morris 2009; Ouyang 2009; Prudden 2009; Li 2010). DNA double-strand breaks (DSBs) are the most dangerous form of DNA damage, and lead to cell death if left unrepaired (FIG. 2) (Darzynkiewicz 2009). Upon DSB formation, the histone protein H2AX is phosphorylated, resulting in recruitment of several DNA damage signaling proteins to the damage sites, including p53-binding protein 1 (53BP1) and ATM (van Attikum 2009). SUMOylation is required for multiple steps in DNA repair pathways, including recruitment of signaling and repair proteins to damage sites and enablement of repair protein function. For example, recruitment of 53BP1 to DNA damage sites is dependent on its SUMOylation (Galanty 2009). 53BP1 mediates DNA damage signaling and repair process. p53 is also involved in apoptosis if DNA damage is not repaired. SUMOylation also plays a role in regulating p53 transactivating activity (Stehmeier 2009) and trafficking (Carter 2007).

SUMOylation also directly regulates repair of various types of DNA damage. Recent studies have shown that SUMOylation is required for both major DSB repair pathways: homologous recombination (HR), in which a homologous sequence acts as a repair template, and non-homologous end joining (NHEJ), in which DSB ends are ligated together (Jeggo 2009). Proteins involved in HR include the well-known breast cancer-related genes BRCA1 and BRCA2, as well as other proteins with DNA binding and helicase activities (Jeggo 2009). Proteins that carry out NHEJ include Ku70, Ku80, DNA-PKcs, XRCC4, XLF, and Artemis (Jeggo 2009). Many proteins in the DSB repair pathways are substrates of SUMOylation (FIG. 2) (Doksani 2009; Morris 2009; Bartek 2010; Li 2010). SUMOylation is also important for response to single-stranded DNA damage (Pfander 2005) and nucleotide base excision repair (Steinacher 2005; Mohan 2007) by modifying repair enzymes to regulate their activity and life spans. These findings suggest that inhibition of SUMO-dependent processes can inhibit repair of a wide range of DNA damage in cancer cells, thereby sensitizing tumor cells to genotoxic stress induced by CRT.

SUMOylation is required for DNA repair, as evidenced by the observation that cells defective in SUMOylation are sensitive to DNA damage reagents (al-Khodairy et al. 1995; Shayeghi et al. 1997). Recently, two independent studies have identified the yeast protein, Mms21, as the SUMO E3 ligase required for repair of both DNA alkylation damage and double-strand breaks (Andrews et al. 2005; Zhao & Blobel 2005). Elimination of Mms21's SUMO E3 activity leads to DNA damage sensitivity. However, the SUMOylation targets in the DNA damage response are not yet well established, nor is SUMOylation's involvement in DNA repair or other cellular functions. Recent studies have shown that a SUMO-targeted ubiquitin ligase (STUBL) is important in DNA damage response, and the ligase specifically recognizes poly-SUMO-2/3 chains to ubiquitinate poly-SUMO modified proteins for degradation (Burgess et al. 2007; Ii et al. 2007; Prudden et al. 2007; Nagai et al. 2008; Cook et al. 2009; Sun et al. 2007).

The enzymes catalyzing SUMO-modification (E1, E2, E3) are present in higher levels in cancer tissues versus normal tissues and in metastasized tumors versus normal cells, and play an important role in cancer proliferation and metastasis. Recent studies suggest that E1 presents an ideal target for the development of cancer therapeutics with specific genetic backgrounds. For example, a genome-wide siRNA screen identified the genes encoding the SUMO E1 subunits SAE1 and SAE2 among those genes with the strongest synthetic lethal interactions with KRas (Luo 2009).

DeSUMOylation enzymes are also thought to be important in cancer. Increased levels of a deSUMOylation isopeptidase (Senp1)) have been observed in prostate cancer, and suppression of Senp1 level by siRNA has been shown to suppress prostate cancer and angiogenesis. Hypoxia also induces high levels of SUMO-1. SUMO-mediated protein-protein interactions appear to be involved in most SUMO-dependent processes.

Given the role of SUMOylation in cancer and other disease states such as viral infection, there is a need in the art for novel SUMOylation enzyme inhibitors. Such inhibitors would be useful both as therapeutics and as research tools for studying the role of SUMOylation in cellular regulation.

SUMMARY

According to the embodiments described herein, a SUMOylation inhibitor compound is provided. The SUMOylation inhibitor compound may have a structure comprising:

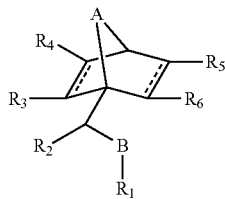

and the pharmaceutically acceptable derivative, solvates, salts and stereoisomers thereof, including mixtures thereof in all ratios, wherein:
  A is O, S, $NR_7$ where $R_7$ is H, alkyl, haloalkyl, alcoxyalkyl, aryl, heteroaryl, cycloalkyl, heterocyclyl, benzyl, alkyl-aryl where $R_7$ is optionally substituted with one to four $R_8$ groups, $CH_2$, $CH_2CH_2$, CH=CH;
  B is O, S, $NR_{11}$ where $R_{11}$ is H, alkyl, haloalkyl, alcoxyalkyl, aryl, heteroaryl, cycloalkyl, heterocyclyl, benzyl, alkyl-aryl where $R_{11}$ is optionally substituted with one to four $R_8$ groups;
  $R_1$ is H, alkyl, haloalkyl, alcoxyalkyl, aryl, heterocyclyl, heteroaryl, cycloalkyl, benzyl, alkyl-aryl where $R_1$ is optionally substituted with one to four $R_8$ groups;
  $R_2$ is H, alkyl, haloalkyl, alcoxyalkyl, aryl, heterocyclyl, heteroaryl, cycloalkyl, benzyl, alkyl-aryl where $R_2$ is optionally substituted with one to four $R_8$ groups;
  $R_3$ is —C(O)—$OR_9$, CN, —C(O)—$NHR_9$, —C(O)—N($R_9$)$_2$, —$SO_2R_9$ and $R_9$ is H, alkyl, haloalkyl, aryl, heteroaryl where $R_9$ is optionally substituted with one to four $R_8$ groups;
  $R_4$ is —C(O)—$OR_9$, CN, —C(O)—$NHR_9$, —C(O)—N($R_9$)$_2$, —$SO_2R_9$ and $R_9$ is H, alkyl, haloalkyl, aryl, heteroaryl where $R_9$ is optionally substituted with one to four $R_8$ groups;
  $R_5$ is H, alkyl, haloalkyl, alcoxyalkyl, aryl, heterocyclyl, heteroaryl, cycloalkyl, benzyl, alkyl-aryl where $R_5$ is optionally substituted with one to four $R_8$ groups;
  $R_6$ is H, alkyl, haloalkyl, alcoxyalkyl, aryl, heterocyclyl, heteroaryl, cycloalkyl, benzyl, alkyl-aryl where $R_6$ is optionally substituted with one to four $R_8$ groups; and
  $R_8$: is halo, —$OR_{10}$, —N($R_{10}$)$_2$, —$SR_{10}$, —$SO_2R_{10}$, —$S(O_2)N(R_{10})_2$, —$S(O)_2OR_{10}$, —$N(R_{10})S(O)_2R_{10}$, —$OS(O)_2R_{10}$, —$C(O)R_{10}$, —$C(O)OR_{10}$, —$C(O)N(R_{10})_2$, —$OC(O)R_{10}$, —$OC(O)OR_{10}$, —$OC(O)N(R_{10})_2$, —$N(R_{10})C(O)R_{10}$, —$N(R_{10})C(O)OR_{10}$, —$N(R_{10})C(O)N(R_{10})_2$, —CN, —$NO_2$, alkyl, haloalkyl, alkyl-$OR_{10}$, or alkyl-$N(R_{10})_2$, where each $R_{10}$ is independently of H, alkyl, haloalkyl, cycloalkyl, heterocyclyl, aryl or heteroaryl.

In other embodiments, the SUMOylation inhibitor compound may have a structure comprising:

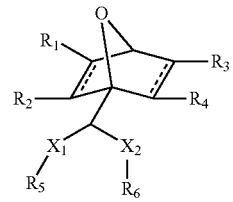

and pharmaceutically acceptable derivatives, solvates, salts and stereoisomers thereof, including mixtures thereof in all ratios, wherein:
  wherein $R_1$, $R_2$, $R_3$ and $R_4$ are selected from the group consisting of H, and —C(O)—O—$R_7$;
  wherein $X_1$ and $X_2$ are selected from the group consisting of C, N, O, S, and P;
  wherein $R_5$ and $R_6$ are selected from the group consisting of alkyl, alkenyl, alkynyl, aryl, and heteroaryl; and
  wherein $R_7$ is alkyl.

In another embodiment, the SUMOylation inhibitor compound has a structure comprising

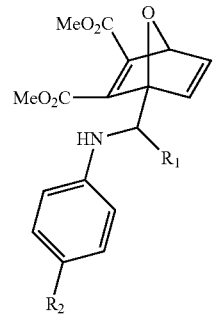

wherein $R_1$ is selected from $CH_2Ph$, $CH_2C_6H_4Me$, $CH_2C_6H_4OMe$, $CH_2C_6H_4F$, $CH_2C_6H_4OF_3$ n-Pr, Allyl, Vinyl or Me; and $R_2$ is selected from H, Cl, Me or OMe. In certain embodiments, the SUMOylation inhibitor compound may be selected from the group having the structure of:

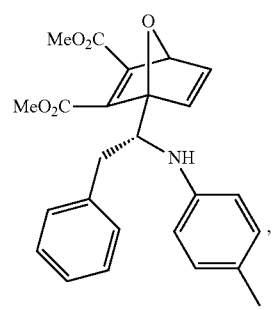

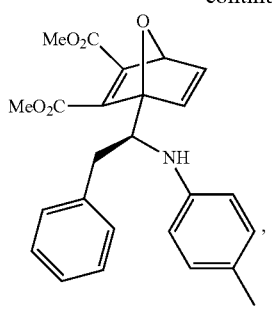
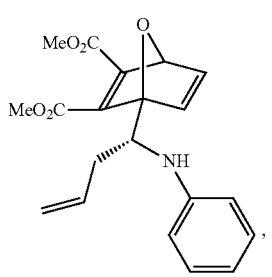
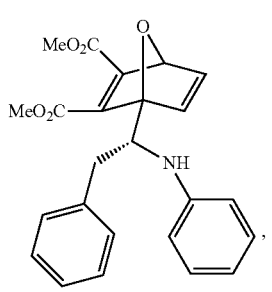
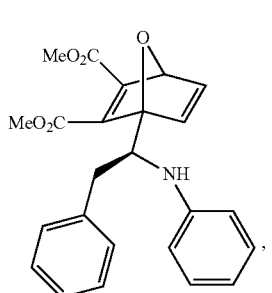
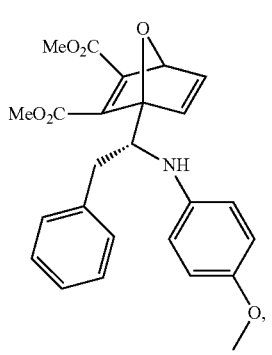
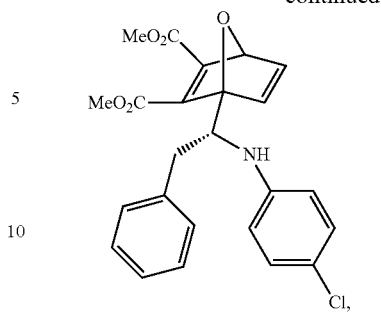
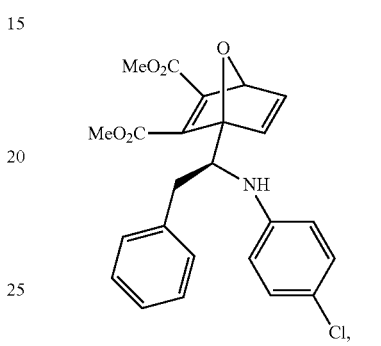
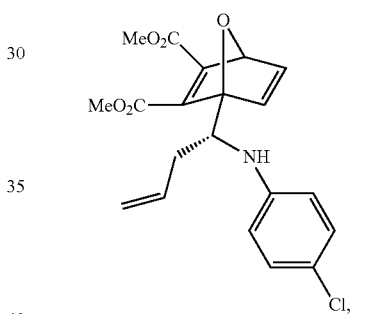
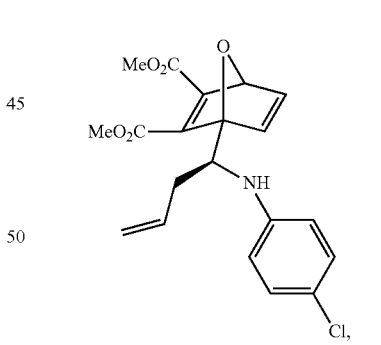
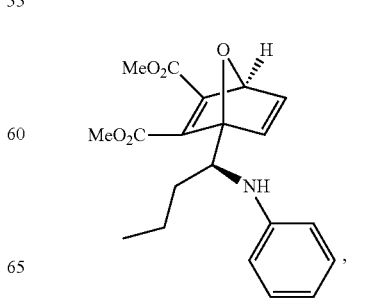

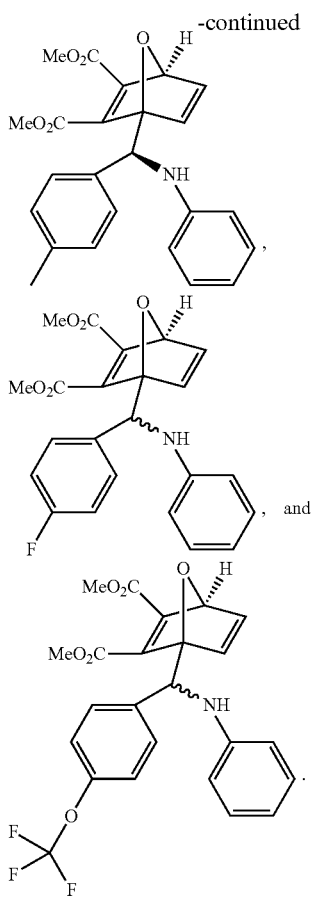

In some embodiments, a method for inhibiting a SUMOylation enzyme in a cell is provided. Such a method may include administering a SUMOylation inhibitor compound, such as those described above, to the cell. In some aspects, the SUMOylation enzyme is SUMO E1 or SUMO E2. In some aspects, the method may be used to inhibit a cancer cell in vitro (e.g., grown in culture) or in vivo (e.g., as part of a tumor in a subject).

In other embodiments, a method for treating a cancer is provided. Such a method may include administering an effective amount of a pharmaceutical composition to a subject having the cancer. The pharmaceutical composition may include a SUMOylation inhibitor compound, such as those described above. In some aspects of this embodiment, the cancer may be any cancer associated with an overexpression or underexpression of a SUMO or SUMOylation enzyme or is associated with SUMOylation of a specific protein. Examples of cancer that may be treated according to the embodiments described herein may include, but are not limited to, colorectal cancer, pancreatic cancer, bone cancer or breast cancer.

In some embodiments, the method for treating a cancer may further comprise administering one or more DNA-damaging therapy in combination with administration of the pharmaceutical composition. Examples of DNA damaging therapies that may be administered in accordance with the embodiments of the disclosure include, but are not limited to, an ionizing radiation source or a chemotherapeutic agent selected from an alkylating agent, platinum analogue or other alkylating-like or nonclassical alkylating agent; an intercalating agent; a topoisomerase inhibitor; or a cytotoxic antibiotic.

BRIEF DESCRIPTION OF THE DRAWINGS

FIG. 3 illustrates the characterization of a singleton probe used to generate E1 enzyme inhibitors. Preliminary structure-activity relationship (SAR) information of a chemical scaffold that contains very potent inhibitors is described. (A) shows a lead compound of this series. (B) shows a summary of SAR information from modifications of two R groups. A total of 37 analogues were made initially.

FIG. 11 illustrates the effect of administering singleton SUMO E1 inhibitor MLS-0437113 on colon cancer cells HT-116 (FIG. 11B) and HT-29 (FIG. 11C) in combination with irradiation treatment at various time intervals as shown. As shown in FIG. 11A, the inhibitor was administered prior to irradiation treatment, and cell viability was measured two days later.

FIG. 13 is a table illustrating SUMO inhibitors that were developed in accordance with some embodiments of the singleton scaffolds described herein. The inhibitors were tested to determine information regarding the structure-activity relationships as shown.

DETAILED DESCRIPTION

Figure 1:
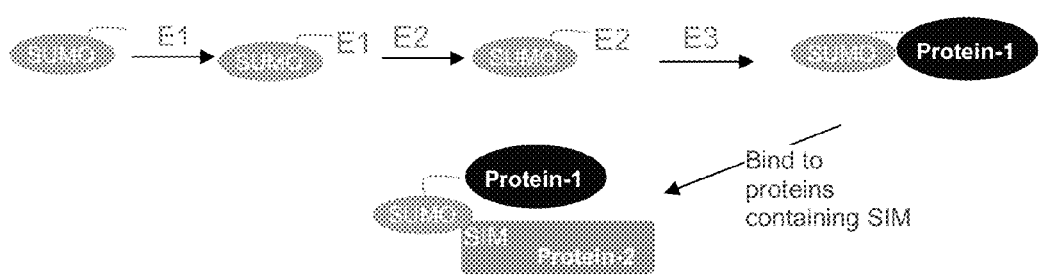
FIG. 1 illustrates the three aspects of the SUMO-mediated processes as they relate to human health. The enzymatic pathway of SUMOylation and a diagram of SUMO-dependent protein complex formation.
Figure 2:
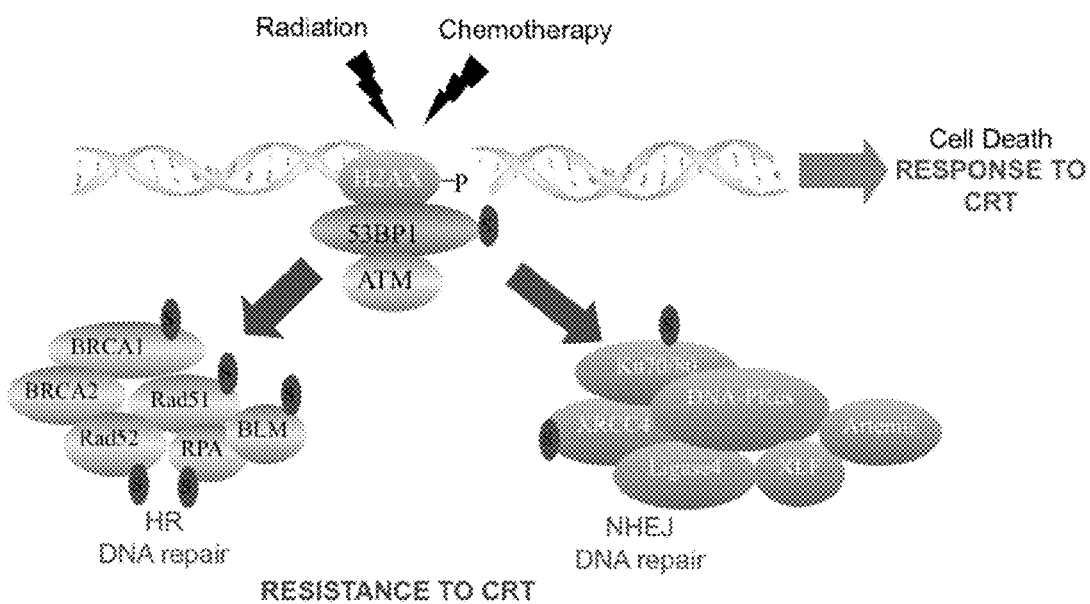
FIG. 2 illustrates the role of SUMOylation in response to a DNA double-strand break in response to chemo- and radiation therapy (CRT). A schematic of current knowledge of the DNA damage signaling and repair pathways for DSBs is shown. Red ovals mark proteins known to be modified by SUMO-1, SUMO-2 or SUMO-3. SUMOylation not only controls events upstream of the repair pathways, but is important for both HR and NHEJ repair pathways. Although not depicted here, SUMOylation is also important for single-stranded DNA repair, regulating nuclease stability, inhibition of the formation of cruciform DNA upon damage, and nucleotide base excision repair.

Provided herein are small molecule inhibitors of SUMOylation enzymes or pharmaceutically acceptable derivatives thereof, as well as various methods of identifying, making and using these inhibitors. Uses for the SUMOylation enzyme inhibitors described herein include, but are not limited to, methods for modulating radiation sensitivity of cancer cells, killing cancer cells and treating diseases and conditions such as cancer and other neoplastic conditions, hereditary diseases and degenerative diseases.

The term "SUMOylation inhibitor" or "SUMO inhibitor" as used herein refers to any small molecule inhibitor that binds one or more subunit of a SUMOylation enzyme, thereby inhibiting the addition of a SUMO protein to a target protein. Such small molecule inhibitors may also inhibit one or more SUMOylation enzymes. The SUMOylation inhibitors, as further described in the studies described herein, have a high level of specificity to SUMO enzymes, thereby affecting SUMOylation, but do not bind or have very low level or negligible binding to proteins found in the ubiquitination pathway. The term "SUMOylation enzyme" or "SUMO enzyme" as used herein refers to SUMO activation enzyme E1, SUMO conjugating enzyme E2 or any one or more of approximately ten SUMO E3 ligases.

In some embodiments, the SUMO inhibitors described herein are SUMO E1 inhibitors. The term "SUMO E1" as used herein refers to SUMO activating enzyme E1, which is made up of subunits SAE1 and SAE2/Uba2. In certain embodiments, the small molecule SUMO E1 inhibitors disclosed herein inhibit both E1 subunits, SAE1 and SAE2. In these embodiments, the inhibitors may inhibit one subunit to a greater degree than the other, or they may inhibit the two subunits equally. In other embodiments, the inhibitors inhibit one subunit only. The SUMO E1 inhibitors may also inhibit SUMO E2. The term "SUMO E2" as used herein refers to SUMO conjugating enzyme E2, which is made up of a single subunit, Ubc9. In certain embodiments, the small molecule SUMO inhibitors described herein inhibit Ubc9 only, or the inhibitors may inhibit Ubc9 and one or more E1 subunits. In these embodiments, the inhibitors may inhibit Ubc9 to a greater degree than the one or more E1 subunits, or they may inhibit two or more of the subunits equally.

Increased expression of SUMO enzymes may contribute to cancer, tumors, or other neoplastic conditions, viral infection, degenerative diseases, genetic or hereditary diseases, or other pathological conditions or diseases. Many cancers have been shown to be associated with increased levels of SUMO enzymes. For example, as discussed in detail in the Examples below, SUMO E1 was found to be the most elevated SUMO enzyme in colorectal cancer tissue, and these high levels of SUMO E1 were associated with radioresistance in colorectal cancer as well as several other types of cancer. (Wiatrek et al. Differential expression of small ubiquitin-like modifier family of proteins in patients with colorectal adenocarcinoma; ASCO Abstract, 2011, which is hereby incorporated by reference as if fully set forth herein; see http://www.asco.org/ascov2/Meetings/Abstracts?&vmview=abst_detail_view&confide=103&abstractID=71189). Overexpression of SUMO enzymes have also been observed in other cancer types (Kim & Baek 2006; Mo & Moschos 2005; Martin et al. 2007; Ulrich 2009; Wang & Banerjee 2004; Mo et al. 2005; Wu & Mo 2007).

Colorectal cancer is the second leading cause of cancer death in the United States (Burt 2009), and CRT is frequently used against colorectal cancer as a preoperative treatment to facilitate surgical intervention (Watanabe 2008) and improve long-term survival (Garcia-Aguilar 2003). However, only a small percentage (<15%) of patients have a complete response to CRT. Therefore, novel SUMO E1 inhibitors that enhance CRT effects and/or impair tumor viability are needed to improve treatment outcomes, preserve quality of life, and reduce healthcare costs. Such SUMO E1 inhibitors may be similarly useful in other cancers, diseases and conditions associated with overexpression of SUMO E1 (Zhu et al. 2010; Kim et al. 2006; Comerford et al 2003; Cheng et al. 2007; Bergink & Jentsch 2009; Galanty et al. 2009; Morris et al. 2009; Ouyang et al. 2009; Subramaniam et al. 2009; Steffan et al. 2004; Jaber et al. 2009).

Therefore, as disclosed herein, a set of small molecule SUMO E1 inhibitors (or "SUMO inhibitor compounds") have been identified and characterized. These inhibitors, which bind to SUMO E1 with high affinity and specificity, represent the first highly specific small molecule inhibitors of SUMO E1. In some embodiments, the SUMO inhibitors do not bind or have negligible binding affinity and specificity for proteins in the ubiquitination pathway. Based on this disclosure, provided herein in certain embodiments are small molecule inhibitors of SUMO E1.

Singleton Scaffolds

In certain embodiments, the small molecule SUMO inhibitors or pharmaceutically acceptable derivatives thereof provided herein comprise a singleton scaffold. In certain embodiments, the singleton scaffold may comprise a structure of Structure A as set forth below:

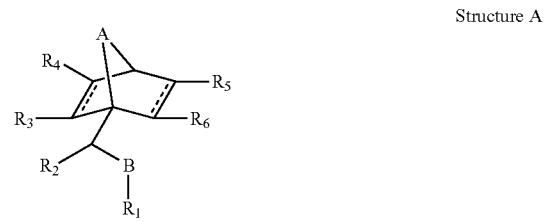

Structure A and the pharmaceutically acceptable derivative, solvates, salts and stereoisomers thereof, including mixtures thereof in all ratios, wherein:

A is O, S, $NR_7$ where $R_7$ is H, alkyl, haloalkyl, alcoxyalkyl, aryl, heteroaryl, cycloalkyl, heterocyclyl, benzyl, alkyl-aryl where $R_7$ is optionally substituted with one to four $R_8$ groups, $CH_2$, $CH_2CH_2$, CH=CH;

B is O, S, $NR_{11}$ where $R_{11}$ is H, alkyl, haloalkyl, alcoxyalkyl, aryl, heteroaryl, cycloalkyl, heterocyclyl, benzyl, alkyl-aryl where $R_{11}$ is optionally substituted with one to four $R_8$ groups;

$R_1$ is H, alkyl, haloalkyl, alcoxyalkyl, aryl, heterocyclyl, heteroaryl, cycloalkyl, benzyl, alkyl-aryl where $R_1$ is optionally substituted with one to four $R_8$ groups;

$R_2$ is H, alkyl, haloalkyl, alcoxyalkyl, aryl, heterocyclyl, heteroaryl, cycloalkyl, benzyl, alkyl-aryl where $R_2$ is optionally substituted with one to four $R_8$ groups;

$R_3$ is —O(O)—$OR_9$, CN, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;

$R_4$ is —O(O)—$OR_9$, CN, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;

$R_5$ is H, alkyl, haloalkyl, alcoxyalkyl, aryl, heterocyclyl, heteroaryl, cycloalkyl, benzyl, alkyl-aryl where $R_5$ is optionally substituted with one to four $R_8$ groups;

$R_6$ is H, alkyl, haloalkyl, alcoxyalkyl, aryl, heterocyclyl, heteroaryl, cycloalkyl, benzyl, alkyl-aryl where $R_6$ is optionally substituted with one to four $R_8$ groups; and $R_8$: is halo, —$OR_{10}$, —$N(R_{10})_2$, —$SR_{10}$, —$SO_2R_{10}$, —$S(O_2)N(R_{10})_2$, —$S(O)_2OR_{10}$, —$N(R_{10})S(O)_2R_{10}$, —$OS(O)_2R_{10}$, —$C(O)R_{10}$, —$C(O)OR_{10}$, —C(O)N$(R_{10})_2$, —$OC(O)R_{10}$, —$OC(O)OR_{10}$, —OC(O)N$(R_{10})_2$, —$N(R_{10})C(O)R_{10}$, —$N(R_{10})C(O)OR_{10}$, —$N(R_{10})C(O)N(R_{10})_2$, —CN, —$NO_2$, alkyl, haloalkyl, alkyl-$OR_{10}$, or alkyl-$N(R_{10})_2$, where each $R_{10}$ is independently of H, alkyl, haloalkyl, cycloalkyl, heterocyclyl, aryl or heteroaryl.

In certain embodiments, the singleton scaffold may comprise a structure of Structure B as set forth below:

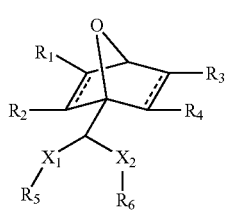

Structure B and the pharmaceutically acceptable derivative, solvates, salts and stereoisomers thereof, including mixtures thereof in all ratios, wherein:

$R_1$, $R_2$, $R_3$ and $R_4$ are independently selected from the group consisting of H, and —C(O)—O—$R_7$;

$X_1$ and $X_2$ are independently selected from the group consisting of C, N, O, S, and P;

$R_5$ and $R_6$ are independently selected from the group consisting of alkyl, alkenyl, alkynyl, aryl, and heteroaryl; and $R_7$ is alkyl.

In one embodiment, the compound comprising a structure of Structure B, and the pharmaceutically acceptable derivative, solvates, salts and stereoisomers thereof, including mixtures thereof in all ratios, wherein:

$R_1$ and $R_2$ are —C(O)—O—$R_7$;

$R_3$ and $R_4$ are H;

$X_1$ is C or N;

$X_2$ is C or N;

$R_5$ is alkyl, alkenyl, or aryl;

$R_6$ is aryl; and $R_7$ is alkyl.

In a more preferred embodiment, the compound comprising a structure of Structure A, and the pharmaceutically acceptable derivative, solvates, salts and stereoisomers thereof, including mixtures thereof in all ratios, wherein:

$R_1$ and $R_2$ are —C(O)—O—$R_7$;

$R_3$ and $R_4$ are H;

$X_1$ is C;

$X_2$ is N;

$R_5$ is ethyl, ethylenyl, phenyl or phenyl substituted with alkyl, halo, haloalkoxy, perfluoroalkoxy, or alkoxy;

$R_6$ is phenyl, phenyl or phenyl substituted with alkyl, halo, haloalkoxy, perfluoroalkoxy, or alkoxy; and $R_7$ is methyl.

In certain of these embodiments, the inhibitors comprise a singleton scaffold having the structure of Structure C as set forth below:

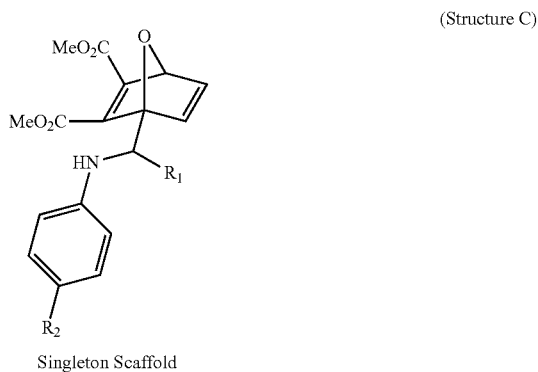

(Structure C)

Singleton Scaffold

Figure 12:
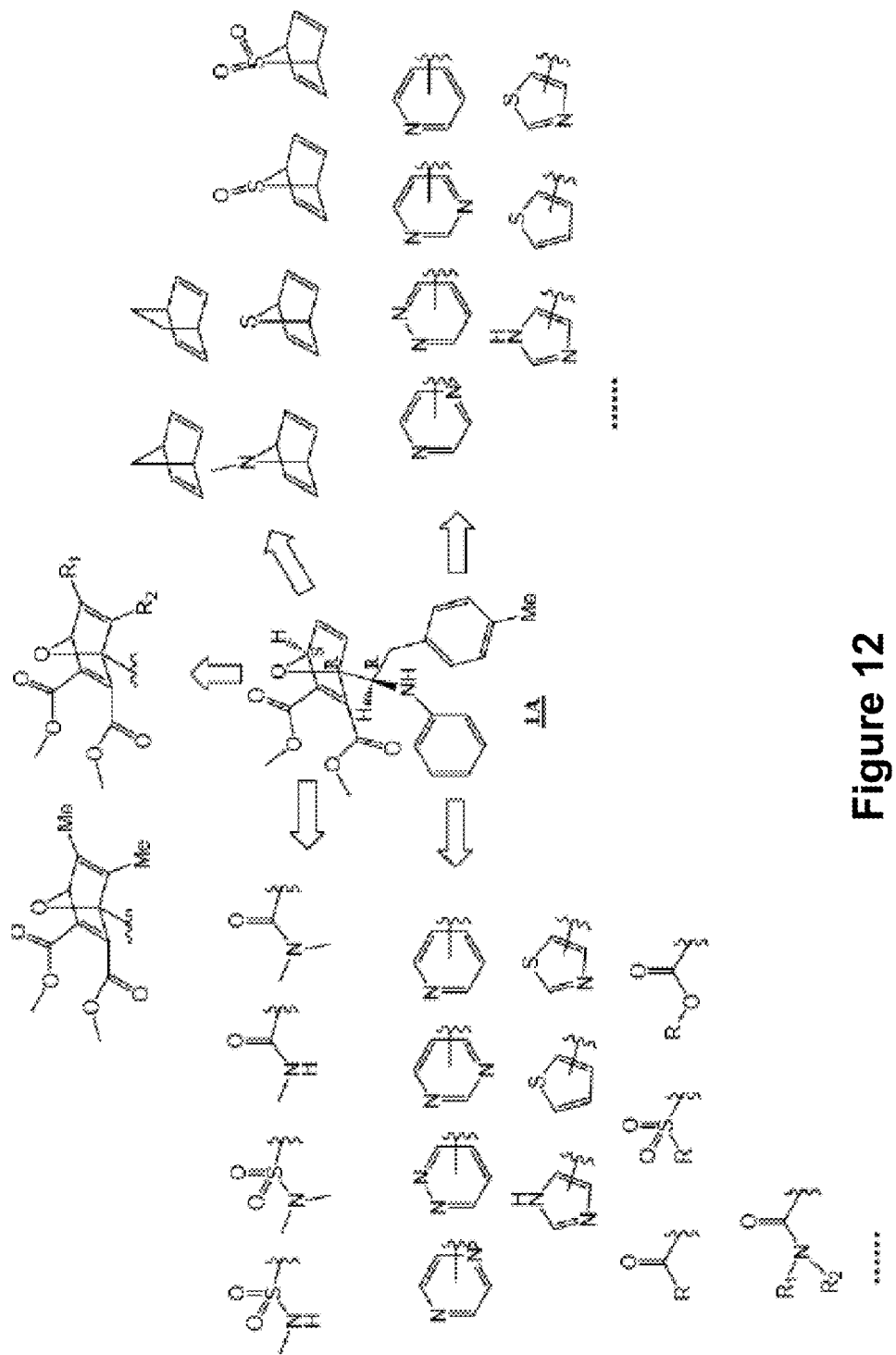
FIG. 12 shows additional functional groups and derivatives that may be used in the singleton scaffold according to some embodiments.

According to some embodiments, the functional groups of the singleton scaffold, $R_1$ and $R_2$, are selected according their ability to increase the inhibitory activity of said scaffold. In some embodiments, $R_1$ is selected from $CH_2Ph$, $CH_2C_6H_4Me$, $CH_2C_6H_4OMe$, $CH_2C_6H_4F$, $CH_2C_6H_4OF_3$ n-Pr, Allyl, Vinyl or Me. In other embodiments, $R_2$ is selected from H, Cl, Me or OMe. Moreover, the $R_1$ and $R_2$ groups may be modified based on identification of a functional group that exhibits enhanced binding affinity toward the SUMO enzyme binding site. Additional functional groups and derivatives thereof are shown in FIG. 12.

In certain of these embodiments the SUMO inhibitors or pharmaceutically acceptable derivatives thereof comprise a structure selected from one or more of the following structures or a functional derivative thereof set forth in Table 1 below:

TABLE 1
Singleton SUMO E1 inhibitors
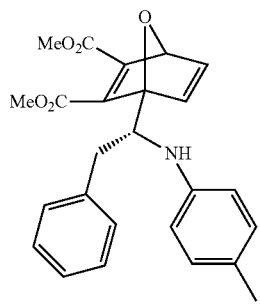 [SMILES: COC(=O)C1=C(C(=O)OC)C2([C@@H](Cc3ccccc3)Nc3ccc(C)cc3)C=CC1O2]
Singleton Analog 1
MLS-0437109
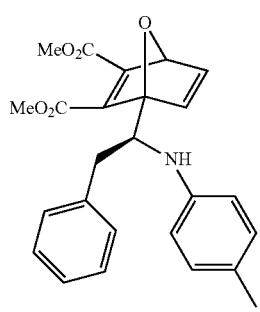 [SMILES: COC(=O)C1=C(C(=O)OC)C2([C@H](Cc3ccccc3)Nc3ccc(C)cc3)C=CC1O2]
Singleton Analog 2
MLS-0437110
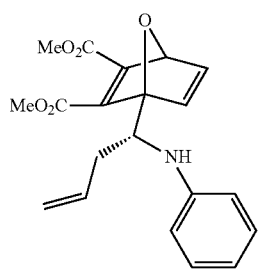 [SMILES: C=CC[C@@H](Nc1ccccc1)C12C=CC(O1)C(C(=O)OC)=C2C(=O)OC]
Singleton Analog 3
MLS-0437111
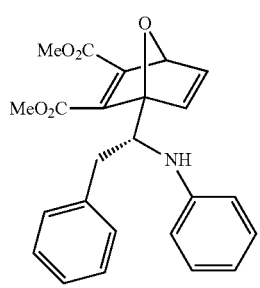 [SMILES: COC(=O)C1=C(C(=O)OC)C2([C@@H](Cc3ccccc3)Nc3ccccc3)C=CC1O2]
Singleton Analog 4
MLS-0437113
TABLE 1-continued
Singleton SUMO E1 inhibitors
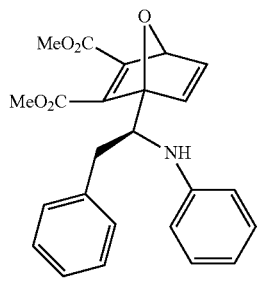 [SMILES: COC(=O)C1=C(C(=O)OC)C2([C@H](Cc3ccccc3)Nc3ccccc3)C=CC1O2]
Singleton Analog 5
MLS-0437114
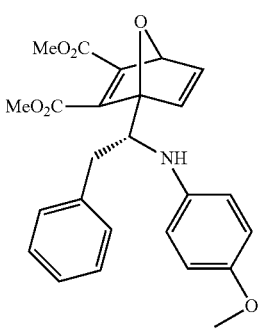 [SMILES: COC(=O)C1=C(C(=O)OC)C2([C@@H](Cc3ccccc3)Nc3ccc(OC)cc3)C=CC1O2]
Singleton Analog 6
MLS-0437118
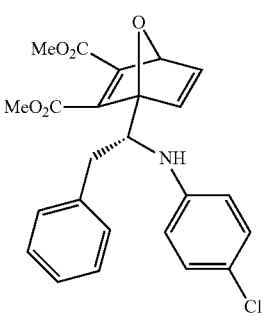 [SMILES: COC(=O)C1=C(C(=O)OC)C2([C@@H](Cc3ccccc3)Nc3ccc(Cl)cc3)C=CC1O2]
Singleton Analog 7
MLS-0437120
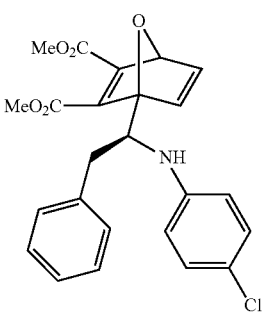 [SMILES: COC(=O)C1=C(C(=O)OC)C2([C@H](Cc3ccccc3)Nc3ccc(Cl)cc3)C=CC1O2]
Singleton Analog 8
MLS-0437121

TABLE 1-continued

Singleton SUMO E1 inhibitors

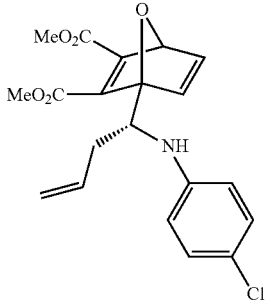 [SMILES: C=CC[C@@H](Nc1ccc(Cl)cc1)C12C=CC(O1)C(C(=O)OC)=C2C(=O)OC]

Singleton Analog 9
MLS-0437126

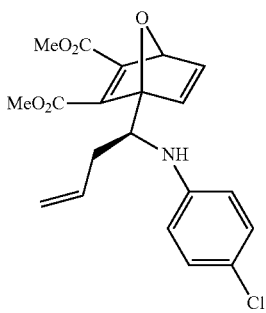 [SMILES: C=CC[C@H](Nc1ccc(Cl)cc1)C12C=CC(O1)C(C(=O)OC)=C2C(=O)OC]

Singleton Analog 10
MLS-0437127

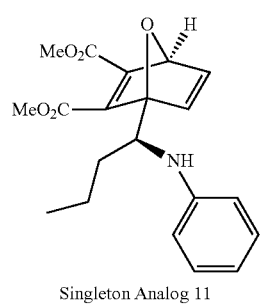

Singleton Analog 11
MLS-0437313

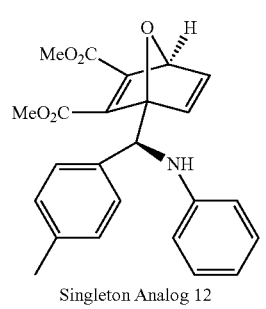

Singleton Analog 12
MLS-0437317

TABLE 1-continued

Singleton SUMO E1 inhibitors

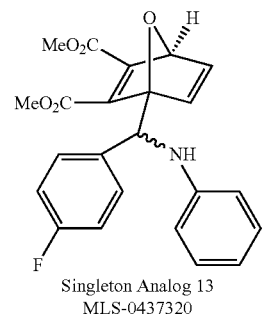

Singleton Analog 13
MLS-0437320

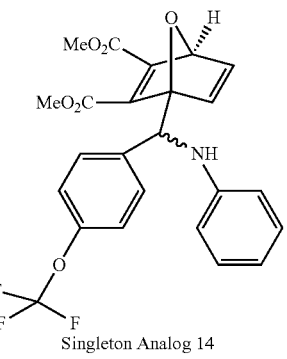

Singleton Analog 14
MLS-0437321

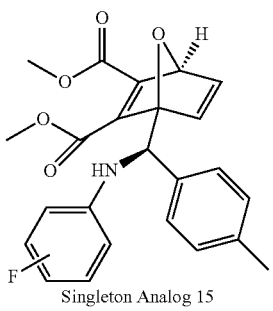

Singleton Analog 15

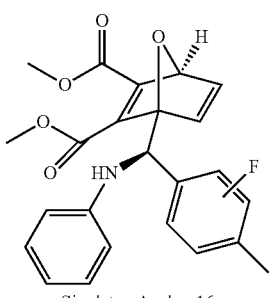

Singleton Analog 16

As used herein, the term "alkyl" refers to a straight or branched chain hydrocarbon having from one to twelve carbon atoms, optionally substituted with substituents selected from the group consisting of C1-C6 alkyl, C1-C6 alkoxy, C1-C6 alkylsulfanyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, when the term "C1-C6" is used to describe a group, it refers to the group containing at least 1, and at most 6, carbon atoms. For example, the term "C1-C6 alkyl" include, but are not limited to, methyl, ethyl, n-propyl, isopropyl, isobutyl, n-butyl, t-butyl, n-pentyl and isopentyl.

As used herein, the term "alkenyl" refers to a straight or branched chain hydrocarbon having from two to twelve carbon atoms and at least one carbon-carbon double bond, optionally substituted with substituents selected from the group consisting of C1-C6 alkyl, C1-C6 alkoxy, C1-C6 alkylsulfanyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Examples of "alkenyl" as used herein include, but are not limited to, ethenyl, n-propenyl, isopropenyl, n-butenyl, isobutenyl, t-butenyl, n-pentenyl, isopentenyl, and the like.

As used herein, the term "alkynyl" refers to a straight or branched chain hydrocarbon having from two to twelve carbon atoms and at least one carbon-carbon triple bond, optionally substituted with substituents selected from the group consisting of C1-C6 alkyl, C1-C6 alkoxy, C1-C6 alkylsulfanyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Examples of "alkyl" as used herein include, but are not limited to, ethynyl, n-propynyl, n-butynyl, isobutynyl, t-butynyl, n-pentynyl, isopentynyl, and the like.

As used herein, the term "halogen" or "hal" refers to fluorine (F), chlorine (Cl), bromine (Br) or iodine (I).

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include C1-C6 alkyl, C1-C6 alkoxy, C1-C6 alkylsulfanyl, C1-C6 alkylsulfenyl, C1-C6 alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, C1-C6 perfluoroalkyl or C1-C6 perfluoroalkoxy, heteroaryl, or aryl, multiple degrees of substitution being allowed. Examples of "aryl" groups include, but are not limited to phenyl, 2-naphthyl, 1-naphthyl, biphenyl, as well as substituted derivatives thereof.

As used herein, the term "heteroaryl" refers to a monocyclic five to seven-membered aromatic ring, or to a fused bicyclic aromatic ring system comprising two of such monocyclic five to seven-membered aromatic rings. These heteroaryl rings contain one or more nitrogen, sulfur and/or oxygen heteroatoms, where N-oxides and sulfur oxides and dioxides are permissible heteroatom substitutions and may be optionally substituted with up to three members selected from a group consisting of C1-C6 alkyl, C1-C6 haloalkyl, C1-C6 haloalkoxy, C1-C6 alkoxy, C1-C6 alkylsulfanyl, C1-C6 haloalkylsulfanyl, C1-C6 alkylsulfenyl, C1-C6 alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, C1-C6 perfluoroalkyl or C1-C6 perfluoroalkoxy, heteroaryl or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "haloalkyl" refers to an alkyl group as defined above containing carbon atoms substituted with at least one halogen, halogen being as defined herein. Examples of branched or straight chained "C1-C6 haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "alkoxy" refers to the group RaO—, where Ra is alkyl as defined above. Exemplary C1-C6 alkoxy groups useful in the invention include, but are not limited to methoxy, ethoxy, n-propoxy, isopropoxy, n-butoxy and t-butoxy.

As used herein, the term "haloalkoxy" refers to the group RbO—, wherein Rb is haloalkyl as defined above.

As used herein, the term "alkylsulfanyl" refers to the group $R_A$S—, where $R_A$ is alkyl as defined above.

As used herein, the term "haloalkylsulfanyl" refers to the group $R_D$S—, where $R_D$ is haloalkyl as defined above.

As used herein, the term "alkylsulfenyl" refers to the group $R_A$S(O)—, where $R_A$ is alkyl as defined above.

As used herein, the term "alkylsulfonyl" refers to the group $R_A$SO$_2$—, where $R_A$ is alkyl as defined above.

As used herein, the term "oxo" refers to the group =O.

As used herein, the term "mercapto" refers to the group SH.

As used herein, the term "carboxy" refers to the group COOH.

As used herein, the term "cyano" refers to the group CN.

As used herein, the term "cyanoalkyl" refers to the group $R_B$CN, wherein $R_B$ is alkylen as defined above. Exemplary "cyanoalkyl" groups useful in the invention include, but are not limited to, cyanomethyl, cyanoethyl and cyanoisopropyl.

As used herein, the term "aminosulfonyl" refers to the group SO$_2$NH$_2$.

As used herein, the term "carbamoyl" refers to the group C(O)NH$_2$.

As used herein, the term "sulfanyl" shall refer to the group S—.

As used herein, the term "sulfenyl" shall refer to the group S(O)—.

As used herein, the term "sulfonyl" shall refer to the group S(O)$_2$— or SO$_2$.

As used herein, the term "acyl" refers to the group $R_F$C(O)—, where $R_F$ is alkyl, cycloalkyl or heterocyclyl as defined herein.

As used herein, the term "C3-C7 cycloalkyl" refers to a non-aromatic cyclic hydrocarbon ring having from three to seven carbon atoms and which optionally includes a C1-C6 alkyl linker through which it may be attached. The C1-C6 alkyl group is as defined above. Exemplary "C3-C7 cycloalkyl" groups include, but are not limited to, cyclopropyl, cyclobutyl, cyclopentyl, cyclohexyl and cycloheptyl.

As used herein, the term "heterocyclic" or the term "heterocyclyl" refers to a three to twelve-membered heterocyclic ring having one or more degrees of unsaturation containing one or more heteroatomic substitutions selected from S, SO, SO$_2$, O or N, optionally substituted with substituents selected from the group consisting of C1-C6 alkyl, C1-C6 haloalkyl, C1-C6 haloalkoxy, C1-C6 alkoxy, C$_1$-C$_6$ alkylsulfanyl, C1-C6 haloalkylsulfanyl, C1-C6 alkylsulfenyl, C1-C6 alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, C1-C6 perfluoroalkyl or C1-C6 perfluoroalkoxy, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, pyrrolidine, piperidine, morpholine, tetrahydrothiopyran, tetrahydrothiophene, and the like.

As used herein, the term "aroyl" refers to the group R$_C$C(O)—, where R$_C$ is aryl as defined herein.

As used herein, the term "heteroaroyl" refers to the group R$_E$C(O)—, where R$_E$ is heteroaryl as defined herein.

As used herein, the term "alkoxycarbonyl" refers to the group R$_A$OC(O)—, where RA is alkyl as defined herein.

As used herein, the term "acyloxy" refers to the group R$_F$C(O)O, where R$_F$ is alkyl, cycloalkyl, or heterocyclyl as defined herein.

As used herein, the term "aroyloxy" refers to the group R$_C$C(O)O—, where R$_C$ is aryl as defined herein.

As used herein, the term "heteroaroyloxy" refers to the group R$_E$C(O)O—, where R$_E$ is heteroaryl as defined herein.

As used herein, the term "carbonyl" or "carbonyl moiety" refers to the group C=O.

As used herein, the term "thiocarbonyl" or "thiocarbonyl moiety" refers to the group C=S.

As used herein, the term "amino," "amino group" or "amino moiety" refers to the group NR$_G$R$_G$', wherein R$_G$ and R$_G$', are preferably selected, independently from one another, from the group consisting of hydrogen, alkyl, haloalkyl, haloalkoxy, alkenyl, cycloalkyl, alkylenecycloalkyl, cyanoalkyl, aryl, aralkyl, heteroaryl, acyl and aroyl. If both R$_G$ and R$_G$' are hydrogen, NR$_G$R$_G$' is also referred to as "unsubstituted amino moiety" or "unsubstituted amino group." If R$_G$ and/or R$_G$' are other than hydrogen, NR$_G$R$_G$' is also referred to as "substituted amino moiety" or "substituted amino group."

As used herein, the term "imino" or "imino moiety" refers to the group C=NR$_G$, wherein R$_G$ is preferably selected from the group consisting of hydrogen, alkyl, haloalkyl, haloalkoxy, alkenyl, cycloalkyl, alkylenecycloalkyl, cyanoalkyl, aryl, aralkyl, heteroaryl, acyl and aroyl. If R$_G$ is hydrogen, C=NR$_G$ is also referred to as "unsubstituted imino moiety." If R$_G$ is a residue other than hydrogen, C=NRG is also referred to as "substituted imino moiety."

As used herein, the term "perfluoroalkyl" refers to an alkyl group with all hydrogens replaced by fluorine, e.g. without limitation, —CF$_3$.

As used herein, the term "perfluoroalkoxy" refers to an alkoxyl group with all hydrogens replaced by fluorine, e.g. without limitation, —OCF$_3$.

As used herein, "⚌" refers to a single bond or double bond.

As used herein, the terms "group," "residue" and "radical" or "groups," "residues" and "radicals" are usually used as synonyms, respectively, as it is common practice in the art.

Method for Inhibiting a SUMOylation Enzyme

In some embodiments, the small molecule SUMO inhibitors described herein may be used in methods for inhibiting a SUMOylation enzyme in a cell. Such methods may include a step of administering an effective amount of a SUMO inhibitor compound to the cell.

According to the embodiments described herein, the SUMO inhibitor compound is one or more of the SUMO inhibitors described herein. The SUMO inhibitors may therefore be used in methods for inhibiting a SUMOylation enzyme (e.g., SUMO E1, SUMO E2 or any one or more of the SUMO E3 ligases) in a cell, as provided herein. In some embodiments, such methods for inhibiting a SUMOylation enzyme may include a step of contacting the cell with or administering to the cell, one or more SUMO inhibitors or a pharmaceutically acceptable derivative thereof, described herein.

The cell may be of any cell type that is associated with SUMOylation (e.g., a cell that overexpresses a SUMOylation enzyme, underexpresses a SUMOylation enzyme, or a cell that expresses a specific cellular protein that is SUMOylated in a disease or other physiological or pathological condition). In certain embodiments, the cell type used in the methods for inhibiting a SUMOylation enzyme described herein may be a cell that is part of a population of cells or a biological tissue that is present, in vivo, in a subject having the disease or other physiological or pathological condition. This may include a human or animal patient that develops the disease or other physiological or pathological condition or, alternatively, may include an animal or invertebrate model wherein the disease, or physiological or pathological condition may be induced. In other embodiments, the cell type used in the methods for inhibiting a SUMOylation enzyme described herein may be a primary, secondary or immortal cell line that is grown in culture. In certain aspects of this embodiment, the method may be used in an in vitro or research setting to investigate the role of SUMOylation in the particular cell, disease, or condition.

The term "effective amount" as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, Pa., 2005, which is hereby incorporated by reference as if fully set forth herein.

E1 contains several substrate-binding sites, including the ATP-binding pocket (Lois & Lima 2005), two SUMO-binding surfaces (Lois & Lima 2005, Wang & Chen) and three Ubc9-binding surfaces (Wang et al. 2007; Wang & Chen; Huang et al. 2007). As disclosed herein, the singleton small molecule SUMO inhibitors developed for SUMO E1 inhibit ATP adenylation, and the inhibitors appear to bind an allosteric site by a tight, non-covalent bond as shown by dilution studies and mass spectrometry. But the inhibitors do not likely bind the ATP-binding pocket directly. However, these inhibitors have been shown to be toxic to cancer cells and may be used alone or in combination with other treatments for treatment of cancer or other diseases or conditions to sensitize cells to genotoxic treatments. The inhibitors may also inhibit HIV infectivity. Therefore, in other embodiments, the SUMO inhibitors may be designed and used, in vivo or in vitro, to selectively target, treat and kill cancer cells or virally infected cells.

In another embodiment, inhibition of ATP binding by the singleton SUMO E1 inhibitors disclosed herein makes the inhibitors useful as research probes for identifying and/or monitoring SUMOylation activity in vitro. In such embodiments, the singleton inhibitors may be conjugated to or otherwise associated with a label for use in various cellular assays. Labels that may be used in accordance with these embodiments may include, but are not limited to, radiolabels such as the radionuclides described below and fluorophores, thiol-reactive labels, biotin and hapten derivatives, crosslinking and photoactivatable reagents, avidins and lectins for use with antibodies, enzyme substrates and other suitable fluorescent labels. For additional guidance, see Molecular Probes Handbook, A Guide to Fluorescent Probes and Labeling Technologies, 11$^{th}$ Edition, Invitrogen, 2010. (lain Johnson and Michelle T. Z. Spence, Eds.), which is hereby incorporated by reference as if fully set forth herein. In such embodiments, the SUMO inhibitors may be used as probes in cell culture assays to determine the effect of SUMOylation activity in a particular cell line. To test whether SUMOylation of a protein of interest is involved in a particular function, a labeled SUMO inhibitor may be added to determine whether the output of the assay changes.

Methods for Treating Cancer

Provided herein in certain embodiments are methods for treating a condition or disease with one or more of the SUMO inhibitors (or "SUMOylation inhibitors" or "SUMOylation inhibitor compounds") and the pharmaceutically acceptable derivative, solvates, salts and stereoisomers thereof, including mixtures thereof in all ratios, described herein These methods may include, but are not limited to, administering a therapeutically effective amount of the one or more SUMO inhibitors or pharmaceutically acceptable derivative, solvates, salts and stereoisomers thereof, including mixtures thereof in all ratios to a subject having the condition or disease. In one embodiment, the SUMO inhibitor is a SUMO E1 inhibitor. In certain embodiments, the or one or more SUMO inhibitors may be identified by methods described herein, for example, using a high throughput screening method to identify a SUMO inhibitor followed by biochemical assays to confirm activities and cellular assays to validate the effects of such inhibitors in cells.

As used herein, the term "functionally effective derivative" or "pharmaceutically acceptable derivative" refers to any physiologically functional derivative of a novel SUMO inhibitor disclosed herein. Such derivatives may include pharmaceutically acceptable salts or so-called pro-drug-compounds, for example compounds according to the invention that are derivatized with alkyl groups, acyl groups, sugars or peptides, such as oligopeptides, that are easily degraded or metabolized to the active compounds according to the invention. Such derivatives may include biodegradable polymer derivatives of the compounds according to the embodiments described herein. Suitable polymers and methods for producing biodegradable polymeric derivatives are known in the art. Further, such derivatives include analogs that have substitutions or modifications that one skilled in the art would recognize as having the same, similar or improved function as the SUMO inhibitors described herein. Upon administration to a subject, a functional derivative of a SUMO inhibitor is capable of providing, directly or indirectly, a SUMO inhibitor disclosed herein, an analog of a SUMO inhibitor disclosed herein or an active metabolite thereof. Such derivatives are clear to those skilled in the art, without undue experimentation. For additional guidance, see Burger's Medicinal Chemistry, Drug Discovery and Development, 7th Edition, Wiley-Interscience, 2010, which is incorporated herein by reference as if fully set forth herein to the extent that it teaches physiologically functional derivatives.

As used herein, the term "solvate" refers to a complex of variable stoichiometry formed by a solute (in this invention, a SUMO inhibitor derivative comprising a structure described herein or a salt or physiologically functional derivative thereof) and a solvent. Such solvents for the purpose of the invention may not interfere with the biological activity of the solute. Examples of suitable solvents include, but are not limited to, water, aqueous solution (e.g. buffer), methanol, ethanol and acetic acid. Preferably, the solvent used is a pharmaceutically acceptable solvent. Examples of suitable pharmaceutically acceptable solvents include, without limitation, water, aqueous solution (e.g. buffer), ethanol and acetic acid. Most preferably, the solvent used is water or aqueous solution (e.g. buffer). Examples for suitable solvates are the mono- or dihydrates or alcoholates of the compounds according to the invention.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, mixtures of enantiomers, as well as purified stereoisomers, purified enantiomers, or stereoisomerically enriched mixtures, enantiomerically enriched mixtures. Also included within the scope of the invention are the individual isomers of the compounds represented by the structures described herein as well as any wholly or partially equilibrated mixtures thereof. The invention also covers the individual isomers of the compounds represented by the structures above as mixtures with isomers thereof in which one or more chiral centers are inverted. Also, it is understood that all tautomers and mixtures of tautomers of the SUMO inhibitor compounds described herein are included within the scope of the SUMO inhibitor compounds and preferably the structures and scaffolds corresponding thereto.

Racemates obtained can be resolved into the isomers mechanically or chemically by methods known in the art. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as camphorsulfonic acid. Also advantageous is enantiomer resolution with the aid of a column filled with an optically active resolving agent (for example dinitrobenzoyl phenylglycine); an example of a suitable eluent is a hexane/isopropanol/acetonitrile mixture. The diastereomer resolution mat also be carried out by standard purification processes, such as, for example, chromatography or fractional crystallization. It also possible to obtain optically active SUMO inhibitor compounds by the methods described above by using starting materials which are already optically active.

SUMOylation inhibitors, when used for a short period of time, are unlikely to be toxic to normal (noncancerous) cells that divide slowly. Recent studies have shown that expression of a peptide inhibitor of the down-stream effects of SUMOylation did not induce cytotoxicity in MCF-7 (WT KRas status) cells in the absence of genotoxic stress (Li et al. 2010).

The small molecule SUMO inhibitors and the pharmaceutically or functionally acceptable derivatives, solvates, salts and stereoisomers thereof, including mixture thereof in all ratios provided herein may be used to treat any condition or disease that is associated with altered levels of SUMOylation including, but not limited to, cancer, tumors, neoplastic conditions or syndromes, viral infections (e.g., HIV), degenerative disease and genetic or hereditary diseases. Such diseases may be associated with, for example, an overexpression or underexpression of one or more SUMOylation enzymes or one or more specific proteins that are SUMOylated in the disease or condition. Examples of specific proteins that may be SUMOylated in a disease or condition include, but are not limited to, p53, HDAC, cyclins and other proteins in cancer; SOD1 in amyotrophic lateral sclerosis; ataxin-1 in spinocerebellar ataxia; huntingtin in Huntington's disease; tau, α-synuclein, DJ-1 or other proteins in Parkinson's disease; tau, APP or other proteins in Alzheimer's disease, lamin A in familial dilated cardiomyopathy; IE1 and IE2 in human CMV; and P6-Gag in HIV.

In one embodiment, the small molecule SUMO E1 inhibitors provided herein are used to treat any cancer associated with increased or decreased expression of SUMO enzymes.

Cancers, tumors or other neoplastic conditions or syndromes that may be treated according to the embodiments described herein include, but are not limited to adenoid cystic carcinoma, adrenal gland tumor, amyloidosis, anal cancer, appendix cancer, ataxia-telangiectasia, attenuated familial adenomatous polyposis, Beckwith-Wiedemann syndrome, bile duct cancer, Birt-Hogg-Dube syndrome, bladder cancer, bone cancer, brain tumor, breast cancer, carcinoid tumor, Carney Complex, cervical cancer, childhood cancer (e.g., brain stem glioma, astrocytoma, central nervous system, craniopharyngioma, Desmoplastic Infantile ganglioglioma, ependymoma, Ewings family of tumors, germ cell tumor, acute lymphoblastic leukemia (ALL), acute myeloid leukemia (AML), Hodgkin's lymphoma, Non-Hodgkin's lymphoma, medulloblastoma, neuroblastoma, osteosarcoma, pleuropulmonary blastoma, retinoblastoma, rhabdomyosarcoma, Wilms tumor), colorectal cancer, Cowden syndrome, endocrine tumor, esophageal cancer, eye cancer, eyelid cancer, fallopian tube cancer, familial adenomatous polyposis, familial malignant melanoma, gallbladder cancer, Gardner syndrome, gastrointestinal stromal tumor (GIST), gestational trophoblastic tumor, head and neck cancer, hereditary cancer (e.g., breast, ovarian, diffuse gastric, leiomyomatosis, renal cell, mixed polyposis syndrome, non-VHL clear cell renal cell carcinoma, pancreatitis and papillary renal cell carcinoma), HIV and AIDS-related cancer, islet cell tumor, juvenile polyposis syndrome, kidney cancer, lacrimal gland tumor, laryngeal and hypopharyngeal cancer, leukemias (e.g., acute lymphocytic leukemia (ALL), acute myeloid leukemia (AML), B-cell leukemia, chronic lymphocytic leukemia (CLL), chronic myeloid leukemia (CML), eosinophilic leukemia, T-cell leukemia), Li-Fraumeni syndrome, liver cancer, lung cancer Hodgkins lymphoma, Non-Hodgkin's lymphoma, Lynch syndrome, mastocytosis, melanoma, meningioma, mesothelioma, Muir-Torre syndrome, multiple endocrine neoplasia types 1 and 2, multiple myeloma, myelodysplastic syndromes (MDS), MYH-associated polyposis, nasal cavity and paranasal sinus cancer, nasopharyngeal cancer, neuroendocrine tumor, neurofibromatosis types 1 and 2, nevoid basal cell carcinoma syndrome, oral and oropharyngeal cancer, ovarian cancer, pancreatic cancer, parathyroid cancer, penile cancer, Peutz-Jeghers syndrome, pituitary gland tumor, prostate cancer salivary gland cancer, sarcoma, skin cancer (non-melanoma), small bowel cancer, stomach cancer, testicular cancer, thymoma, thyroid cancer, tuberous sclerosis syndrome, Turcot syndrome, unknown primary cancer, uterine cancer, vaginal cancer, Von Hippel-Lindau syndrome, vulvar cancer, Waldenstrom's macroglobulinemia, Werner syndrome, and xeroderma pigmentosa.

In some embodiments, cancers, tumors or other neoplastic conditions or syndromes that may be treated according to the embodiments described herein include, but are not limited to those that are considered to be responsive to radiation therapy (alone or in combination with one or more other treatments), including, but not limited to, brain cancer, breast cancer, cervical cancer, colorectal cancer, endometrial cancer, head and neck cancer, Hodgkin's disease and local extranodal lymphoma, melanoma, ovarian cancer, prostate cancer, rhabdomyosarcoma, retinoplastoma, skin and lip cancer, soft tissue carcinoma, testicular cancer, thyroid cancer, and Wilms tumor.

In some embodiments, the SUMO inhibitor is part of a pharmaceutical composition. The pharmaceutical composition may include one or more SUMO inhibitor and a pharmaceutically acceptable carrier. In some embodiments, the pharmaceutical composition/SUMO inhibitor may be administered in combination with one or more DNA-damaging therapies. In this case, the SUMO inhibitor may sensitize the target cells/cancer cells to the DNA-damaging therapy. Thus, the DNA-damaging therapy is more effective, and allows the use of lower doses, thereby minimizing or eliminating harm to healthy cells.

The term "treat," "treating" or "treatment" as used herein with regard to a condition or disease may refer to preventing a condition or disease, slowing the onset or rate of development of the condition or disease, reducing the risk of developing the condition or disease, preventing or delaying the development of symptoms associated with the condition or disease, reducing or ending symptoms associated with the condition or disease, generating a complete or partial regression of the condition or disease, or some combination thereof.

A "pharmaceutically acceptable carrier" may refer to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof, described in further detail below. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

Pharmaceutically acceptable carriers are well known in the art and include, for example, aqueous solutions such as water or physiologically buffered saline or other solvents or vehicles such as glycols, glycerol, oils such as olive oil or injectable organic esters, or emulsions such as oil/water emulsions or a triglyceride emulsion, various types of wetting agents, tablets, coated tablets and capsules. A suitable pharmaceutically acceptable carrier may be selected taking into account the chosen mode of administration.

A pharmaceutically acceptable carrier can also contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art will know that the choice of a pharmaceutically acceptable carrier, including a physiologically acceptable compound, depends, for example, on the route of administration of the composition.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder or tablet.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of the SUMO inhibitors described herein the pharmaceutical compositions may also include suitable diluents, preservatives, solubilizers, emulsifiers, adjuvant and/or carriers.

The compound can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Optimal dosages to be administered may be determined by those skilled in the art, and will vary with the particular compound in use, the severity of the disease state, drug combination(s), reaction sensitivities, and response to therapy. Additional factors depending on the particular subject being treated, including the general health of the subject, the age, weight, gender and diet of the subject, and time and frequency of administration, will result in a need to adjust dosages. Administration of the SUMO inhibitors or pharmaceutical composition thereof may be effected continuously or intermittently. In any treatment regimen, the SUMO inhibitors or pharmaceutical composition may be administered to a patient either singly or in a cocktail containing other therapeutic agents, compositions, or the like, including, but not limited to, tolerance-inducing agents, potentiators and side-effect relieving agents. Preferred potentiators include monensin, ammonium chloride, perhexyline, verapamil, amantadine, and chloroquine. All of these agents are administered in generally-accepted efficacious dose ranges such as those disclosed in the Physician's Desk Reference, 41st Ed., Publisher Edward R. Barnhart, N.J. (1987), which is incorporated herein by reference.

The term "subject" may refer to a human or any other animal, animal model or invertebrate model having a condition, a disease, a cell, or a population of cells that may be treated or used accordance with the methods or with the compounds or compositions described herein. In one embodiment, the subject is a human subject having a disease or condition, such as those described herein. In other embodiments, the subject is any other animal having such a disease or condition, including an animal model used as a research tool that is developed to have the disease or condition or has one or more aspects, attributes, symptoms, or other variables associated with the disease or condition. As such, the SUMO inhibitors described herein may be used as research tools. Such animals or animal models may include, but are not limited to, mice, rats, rabbits, monkeys, pigs, dogs, cats, and birds. In another embodiment the subject may be any other vertebrate or invertebrate model that can be used as a research tool including, but not limited to, a fish (e.g., zebrafish), an insect (e.g., *drosophila*), nematode (e.g., *c. elegans*), mollusk (e.g., *aplesia californicus*).

In some embodiments, a cell or population of cells grown in culture may be used in accordance with the methods or with the compounds or compositions described herein. The cell or population of cells may be derived from or cultured from one or more subjects described above, and may used as a research tool in accordance with the embodiments described herein.

Administering one or more compounds or compositions described herein to the subject, cell or population of cells to investigate one or more mechanisms or other aspects of a condition or disease described herein; or for investigating the effect of one or more compounds or compositions described herein when administered to the cell, population of cells or subject.

The term "route of administration" or "administering" may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

The singleton SUMO E1 inhibitors characterized herein were not toxic to human hepatocytes at concentrations up to 50 μM (FIG. 10), but induced significant sensitivity to radiation in various cancer cell lines. These findings are particularly important in developing treatment strategies and regimens for increasing the efficacy of radiation therapy, because radiation therapy is delivered locally to tumors, but systemically delivered SUMOylation inhibitors should not cause significant damage to non-irradiated normal cells. Additionally, such inhibitors may be directly applied to rectal cancers locally, an established strategy. Taken together, the studies described herein are significant in that they should lead to development of new paradigms of more effective CRT that are applicable to a wide range of cancers, as well as the first small molecular probes of SUMOylation to elucidate its role in cellular regulation.

Therefore, according to some embodiments, a SUMO inhibitor, alone or as part of a pharmaceutical composition, may be administered in combination with one or more additional therapeutic agents to treat a condition or disease that is associated with altered levels of SUMOylation. In some embodiments, the one or more additional therapeutic agents include one or more DNA-damaging (or "genotoxic") therapy. Administration of the SUMO inhibitor in combination with the one or more genotoxic therapy may increase the efficacy of the one or more additional therapeutic agents, produce a synergistic effect between the inhibitor and the one or more additional therapeutic agents, sensitize cells affected by the condition or disease associated with altered levels of SUMOylation, or a combination thereof.

The term "in combination" or "in combination with" as used herein, means in the course of treating the same disease or condition in a subject using two or more therapies (e.g., agents, drugs, treatment regimens, treatment modalities or a combination thereof) in any order. This includes simultaneous administration (or "co-administration"), administration of a first therapy prior to or after administration of a second therapy, as well as in a temporally spaced order of up to several days apart. Such combination treatment may also include more than a single administration of any one or more therapies. Further, the administration of the two or more therapies may be by the same or different routes of administration.

According to the embodiments described herein, genotoxic therapies that may be administered in combination with the SUMO inhibitors to treat a disease or condition associated with SUMOylation may include, but are not limited to, administration of one or more radiation therapy regimens, administration of one or more DNA-damaging or genotoxic chemotherapeutic agents, or a combination thereof.

Administration of one or more radiation therapy regimens may include any source of ionizing radiation, including x-rays, gamma-rays, alpha particles, beta particles or a combination thereof. These radiation sources may be administered using any sealed source (e.g., external beam radiation therapy, brachytherapy, stereotactic radiation, virtual simulation, 3-dimensional conformal radiation therapy (3DCRT), and intensity modulated radiation therapy (IMRT), image guided radiation therapy (IGRT), particle therapy) or unsealed source (e.g., systemic radioisotope therapy). Examples of radiation sources or imaging methods that may be used according to the embodiments described herein may include, but are not limited to, radiographs, computed tomography (CT), fluoroscopy, positron emission tomography (PET), single photon emission computed tomography (SPECT), radionuclides used alone or with an imaging method such as CT, PET or SPECT (e.g., Barium-133, Cadmium-109, Cobalt-57, Cobalt-60, Iodine-131, Iodine-131methaiodobenzylguanidine (MIBG), Europium-152, Manganese-54, Sodium-22, Zinc-65, Technetium-99m, Polonium-210, Strontium-90, Thallium-204, Carbon-14, Lutetium-177, Yttrium-90, Phosphorus-32, Strontium-89, Samarium-153, Radium-223, Bismuth-213), radioimmunotherapy (e.g., Yttrium ($^{90}$Y) ibritumomab tiuxetan, Iodine ($^{131}$I) tositumomab)

In some embodiments, the one or more genotoxic chemotherapeutic agents that may be administered in combination with the SUMO inhibitors described herein include, but are not limited to, (i) alkylating agents, platinum analogues or other alkylating-like or nonclassical alkylating agents (e.g., carmustine, streptozocin, busulfan, chlorambucil, ifosfamide, cyclophosphamide, thiotepa, lomustine, cisplatin, carboplatin, mechlorethamine, chloambucil, oxaliplatin, uramustine, melphalan, nedaplatin, satraplatin, triplatin tetranitrate, procarbazine, altretamine and temozolomide); (ii) intercalating agents (e.g., doxorubicin, epirubicin, danorubicin, daunomycin, proflavine, ethidium bromide, berberine, thalidomide and dactinomysin); (iii) topoisomerase inhibitors (etopocide, topotecan, irinotecan, amsacrine, camptothecin, lamellarin D, teniposide, aurintricarboxylic acid and HU-331); and (iv) cytotoxic antibiotics (e.g., actinomycin. valrubicin, idarubicin, bleomycin, plicamycin and mitomysin).

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

Example 1

SUMO-1, -2, and -3 Expression in Colorectal Cell Lines

SUMO1, -2, and -3 mRNA levels were measured in the colorectal cancer cell lines HCT116 and HT29, which represent the majority of colorectal cancer types (e.g., they have chromosome instability or are mismatch repair deficient). Specifically, gene expression levels were measured for both SUMO E1 subunits (SAE1 and SAE2); SUMO E2 (Ubc9); the SUMO E3 ligases PIAS1, PIAS2, PIAS3, PIAS4, RanBP2, MMS21; and de-SUMOylation enzymes SENP1, 2, 3, 4, 5, 6, and 7. Expression levels in HCT116 and HT29 were compared to those in normal colon mucosa. GAPDH expression levels were used as a control.

Significantly higher mRNA levels were observed for most SUMOylation-related genes (Table 2). The two E1 subunits (SAE1 and SAE2) were the most elevated, with significantly greater increases in expression than Ubc9 (E2) and PIAS3 (E3). This is significant because Ubc9 and PIAS3 were both previously found to be elevated in many cancer types (Wang 2004; Mo 2005).

TABLE 2

| SUMO-1, -2, and -3 expression in colorectal cell lines | | | | |
|---|---|---|---|---|
| Gene | HCT116 (RPKM*) | HT29 (RPKM*) | Avg. control (RPKM*) | Fold-change in HCT116 vs. control | Fold-change in HT29 vs. control |
| E1 (SAE1) | 103.75 | 108.24 | 17.34 | 5.98 | 6.24 |
| E2 (SAE2) | 60.09 | 91.02 | 6.13 | 9.80 | 14.85 |
| E3 (PIAS3) | 6.64 | 7.95 | 1.53 | 4.34 | 5.20 |
| E2 (Ubc9) | 113.94 | 101.28 | 29.31 | 3.89 | 3.46 |
| GAPDH | 2100.40 | 2313.06 | 1094.17 | 1.92 | 2.11 |

RPKM: reads per kilobase per million mapped

Immunohistochemistry studies were performed on stage II and III colorectal tumor specimens and matched normal tissues. Consistent with the mRNA expression results, SAE1 and SAE2 were the most significantly overexpressed SUMOylation-related proteins in tumor specimens relative to the matched normal tissues (Wiatrek et al. Differential expression of small ubiquitin-like modifier family of proteins in patients with colorectal adenocarcinoma; ASCO Abstract, 2011, which is hereby incorporated by reference as if fully set forth herein; see http://www.asco.org/ascov2/Meetings/Abstracts?&vmview=abst_detail_view&confide=103&abstractID=71189).

SAE1 and SAE2 levels were found to be the only SUMO proteins with increased expression in resistant tumors after CRT in comparison to pretreatment biopsy samples. To validate this clinical observation, a radioresistant HCT116 line was developed by irradiating (2Gy/day) a mouse xenograft tumor for one week, cutting out the xenograft and using it to start a primary culture, then irradiating the culture (2Gy/day) for another week. Comparison of the radioresistant HCT116 line with the parental line showed that the SAE2 level was approximately 3-fold greater in the radioresistant line. The level of other SUMO enzymes did not change significantly.

The results of these studies indicate that upregulated SUMO E1 levels are correlated with a patient's response to CRT, and that the E1 level increases after CRT in resistant tumors.

Example 2

Development of Singleton SUMO E1 Inhibitors

Through the Molecular Library Probe Production Center Network (MLPCN), at least 300,000 compounds were screened using a TR-FRET method, an ALPHASCREEN™ method or both, and tested for their ability to inhibit SUMOylation of a target protein via SUMO E1 or SUMO E2. The assays were based on SUMOylation of the target protein RanGAP1, which is a protein that is efficiently SUMOylated with only the SUMO E1 and E2 enzymes, and does not use E3 ligases. A fluorescence resonance energy transfer (FRET) assay was the primary assay followed by a chemoluminescence-based secondary assay using ALPHA screen to eliminate false positive hits. Then, the hits were screened by a poly-ubiquitination assay using ubiquitin, ubiquitin E1, Ubc5 and Apc11 to eliminate inhibitors not specific to SUMOylation. The screening identified a potent family of SUMOylation inhibitors based on a singleton scaffold (FIG. 3). A lead compound was selected, and is identified herein as MLS0437113 (FIG. 3). Table 1 shows representative compounds of the SUMOylation inhibitors derived from the singleton scaffold.

Initially, 37 analogues (see FIG. 13) were synthesized to further explore this scaffold as summarized in FIG. 3. These analogs were synthesized according to the representative protocol shown in Scheme 1.

Scheme 1:

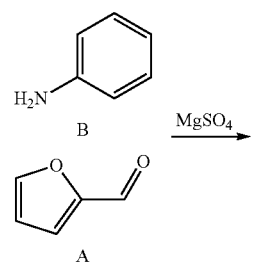

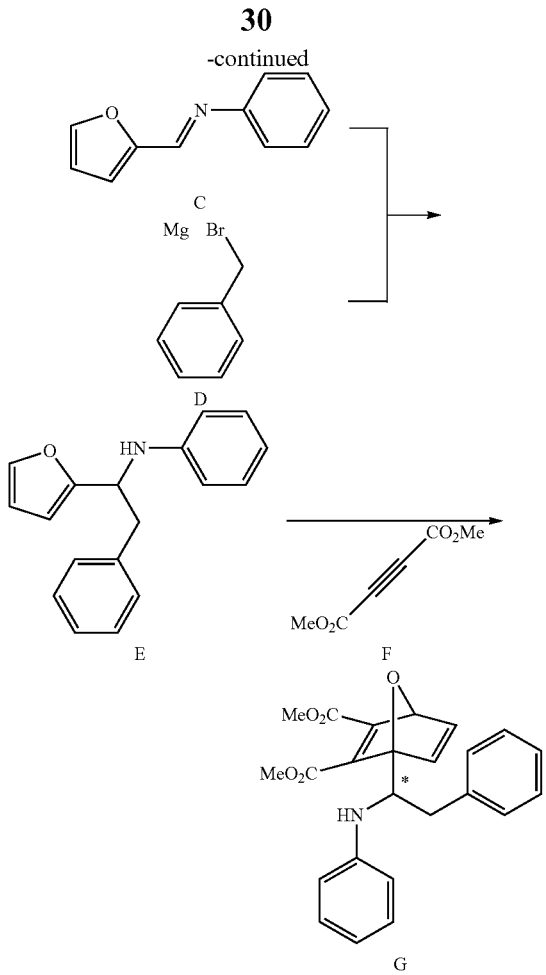

Generation of (E)-N-(Furan-2-ylmethylene)aniline (C)

Furfural (A, 580.0 mg, 6.04 mmol) was placed in a round-bottom flask and dissolved in 7.50 mL dichloromethane. Magnesium sulfate (750 mg, 6.23 mmol, 1.03 equiv) was added to it followed by aniline (B, 660 uL, d 1.02 g/mL, 1.23 mmol, 1.20 equiv) and the reaction mixture was stirred at room temperature for 15 hrs. Upon completion, the drying reagent was filtered off and the residual solvent was removed on the rotary evaporator. The product imine C (883.0 mg, 86% yield) was recovered as volatile red-brown oil that was used without further purification. $^1$H NMR (500 MHz, CDCl$_3$) δ 8.30 (s, 1H), 7.63 (br s, 1H), 7.44-7.36 (m, 2H), 7.30-7.22 (m, 3H), 7.02 (s, 1H), 6.57 (dd, J=3.4, 1.7 Hz, 1H). ($^1$H-NMR: Purity>95%).

Generation of N-(1-(Furan-2-yl)-2-phenylethyl) aniline (E)

Magnesium (755.0 mg, 31.02 mmol, 6.02 equiv) was placed in a round-bottom flask and the vessel and its content was flame-dried under vacuum. When the flask was cooled to room temperature 15.0 mL ethyl ether was added and the flask was placed in an ice bath. Benzyl bromide (D, 1.84 mL, d 1.44 g/mL, 3.00 equiv) was added drop-wise over a 30 min period. A cloudy solution formed and the reaction mixture was stirred for 1 hr while it was slowly warmed up to room temperature. Imine C (883.0 mg, 5.16 mmol) was dissolved in 26.0 mL ethyl ether, added slowly to the resulting mixture and then stirred for 16 hrs before quenching with cold saturated solution of ammonium chloride. The product was extracted with ethyl acetate, dried over magnesium sulfate, and concentrated on a rotary evaporator. The crude oil thus obtained was purified via column chromatography using 1 to 5% gradient of ethyl acetate in hexanes. Aniline E (590 mg, 43%) was recovered as yellow-orange oil. $^1$H NMR (500 MHz, CDCl$_3$) δ 7.41-7.39 (m, 1H), 7.32-7.21 (m, 3H), 7.17 (t, J=7.9 Hz, 2H), 7.09 (d, J=7.2 Hz, 2H), 6.74 (t, J=7.3 Hz, 1H), 6.63 (d, J=8.0 Hz, 2H), 6.30-6.27 (m, 1H), 6.07 (d, J=3.2 Hz, 1H), 4.79 (t, J=6.5 Hz, 1H), 4.06 (br s, 1H), 3.28-3.19 (m, 2H). ($^1$H-NMR: Purity>95%).

Generation of Dimethyl 1-(2-Phenyl-1-(phenylamino)ethyl)-7-oxabicyclo[2.2.1]hepta-2,5-diene-2,3-dicarboxylate (G)

Aniline compound E (300.0 mg, 1.14 mmol) was placed in a vial and dissolved in 7.60 mL toluene. The vial was capped and the solution was brought to reflux. Dimethyl acetylenedicarboxylate (F, 255.0 mL, d 1.16 g/mL, 1.83 equiv) was added in one portion to the hot solution and the vial was capped tightly. The reaction mixture was continued to reflux for 24 hrs after which it was cooled and the solvent was removed on the rotary evaporator. The resulting brown mass containing the product as a diastereomeric mixture (52:48) was purified via centrifugal thin layer chromatography using a Chromatotron™ and 20% ethyl ether in hexanes as an eluent mixture. The major product was assigned configuration R at the marked stereocenter reflecting the appropriate relative stereochemistry (see above). The compound was isolated as a single diastereomer of >95% purity by $^1$H-NMR and LC-MS techniques. $^1$H NMR (500 MHz, CDCl$_3$) δ 7.31-7.23 (m, 4H), 7.23-7.17 (m, 1H), 7.12 (t, J=7.9 Hz, 2H), 7.05 (dd, J=5.3, 1.7 Hz, 1H), 6.68 (t, J=7.3 Hz, 1H), 6.54 (d, J=7.9 Hz, 2H), 6.52 (d, J=5.3 Hz, 1H), 5.79 (d, J=1.7 Hz, 1H), 4.63 (dt, J=13.9, 7.1 Hz, 1H), 4.06 (d, J=10.4 Hz, 1H), 3.78 (s, 3H), 3.43 (s, 3H), 2.98 (m, 2H). $^{13}$C NMR (126 MHz, CDCl$_3$) δ 164.8, 162.5, 156.4, 149.6, 146.4, 143.4, 142.7, 138.1, 129.8, 129.1, 128.2, 126.4, 117.8, 113.2, 101.9, 83.8, 53.2, 52.2, 52.1, 37.7. ($^1$H-NMR: Purity>95%).

Figure 4:
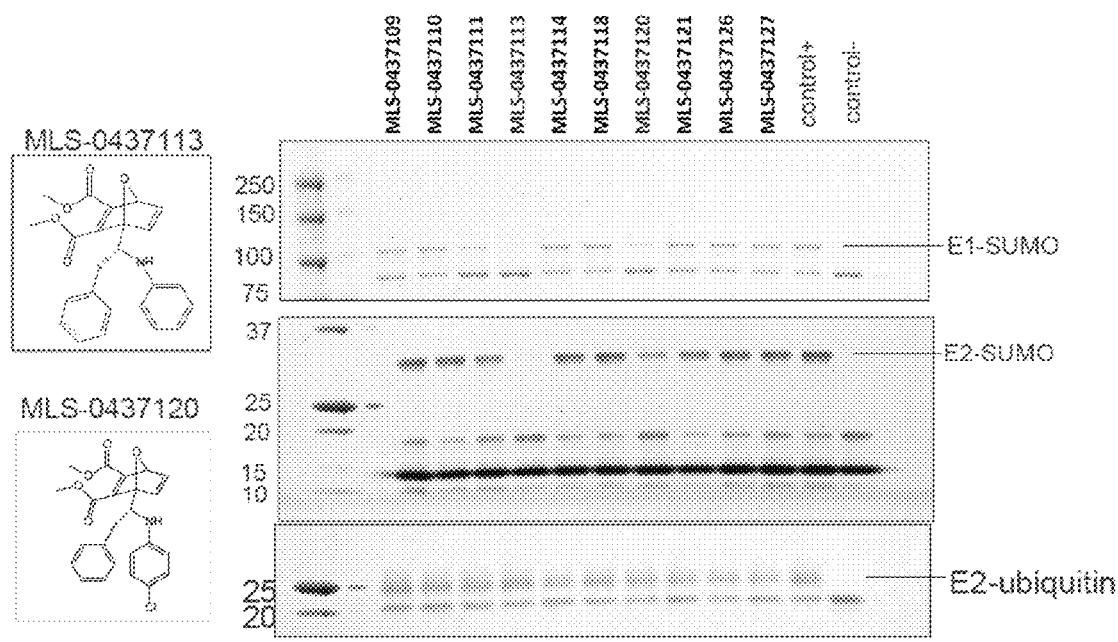
FIG. 4 illustrates a representative assay to determine the efficacy of E1 inhibitors generated from a singleton probe. Stereo-specific effects of this series in inhibiting the SUMO E1. Preliminary biochemical assays demonstrating inhibition of the SUMO E1 as determined by formation of E1-SUMO thioester and E2~SUMO thioester conjugates in the presence of each inhibitor (10 μM). Negative and positive controls were reactions in the absence and presence of ATP. The structures of the two most potent compounds are shown to the left. The compounds that are immediately right to them in the assays, MLS-0437114 and MLS-0437121, are their stereoisomers, respectively. The stereo chemistry was determined by X-ray crystallography. None of these inhibitors inhibited ubiquitination at 100 μM inhibitor concentration.

Each singleton analog was analyzed to determine its inhibitory effect on SUMOylation and ubiquitination, tested both in the HTS format and gel-based format (FIG. 4). The MLS-0437113 analog was the most potent inhibitor in this series (FIG. 4), and was selected as a lead compound. The racemic diastereomer of the MLS-0437113 analog (at the * carbon), MLS-0437114, was significantly less inhibitory, demonstrating a stereo-specific inhibitory effect. The stereo-specific effect is also demonstrated by another pair of analogues: MLS-0437120 and MLS-0437121, which are racemic diastereomers of each other, and MLS-0437120 is more inhibitory than MLS-0437121 (FIG. 4). The stereo-specific inhibitory effect indicates that inhibition is not due to non-specific mechanisms, such as alkylation of catalytic Cys residues. In addition, none of the analogues were inhibitory to ubiquitination assays at up to 100 mM inhibitor concentrations (FIG. 4), further demonstrating that the inhibitory effect is not through a non-specific mechanism, because both the ubiquitin and SUMO E1 contain homologous catalytic centers including catalytic Cys residues and ATP-binding sites. The inhibitory effect of this compound was not affected by addition of BSA, suggesting that it has minimal non-specific binding to other proteins.

The molecular weight (MW), IC$_{50}$, strength of SUMO-RanGap1 and SUMO-E2 conjugation inhibition of the SUMO E1 inhibitors derived from the singleton scaffold (see Table 1 above for structures) generated according to the embodiments herein are shown in Table 3 below.

TABLE 3

| | | | | |
|---|---|---|---|---|
| | | | Singleton E1 Inhibitors | |
| Batch ID | Amt. (mL) | MW | SUMO (AlphaScreen-BSA) IC$_{50}$ (µM) | SUMO-RanGap1 and SUMO-E2 Conjugation Inhibition |
| MLS-0437109.0001 | 0.100 | 419.47 | 6.9 | Weak |
| MLS-0437110.0001 | 0.100 | 419.47 | 9.2 | Very Weak |
| MLS-0437111.0001 | 0.100 | 355.38 | 3.3 | Strong |
| MLS-0437113.0001 | 0.100 | 405.44 | 0.47 | Strong |
| MLS-0437114.0001 | 0.100 | 405.44 | 11.7 | Weak |
| MLS-0437118.0001 | 0.100 | 435.47 | 9.5 | Very Weak |
| MLS-0437120.0001 | 0.100 | 439.89 | 5.2 | Weak |
| MLS-0437121.0001 | 0.100 | 439.89 | 9.2 | Very Weak |
| MLS-0437126.0001 | 0.100 | 389.83 | 12.5 | Weak |
| MLS-0437127.0001 | 0.100 | 389.83 | 11.5 | Weak |

Figure 7:
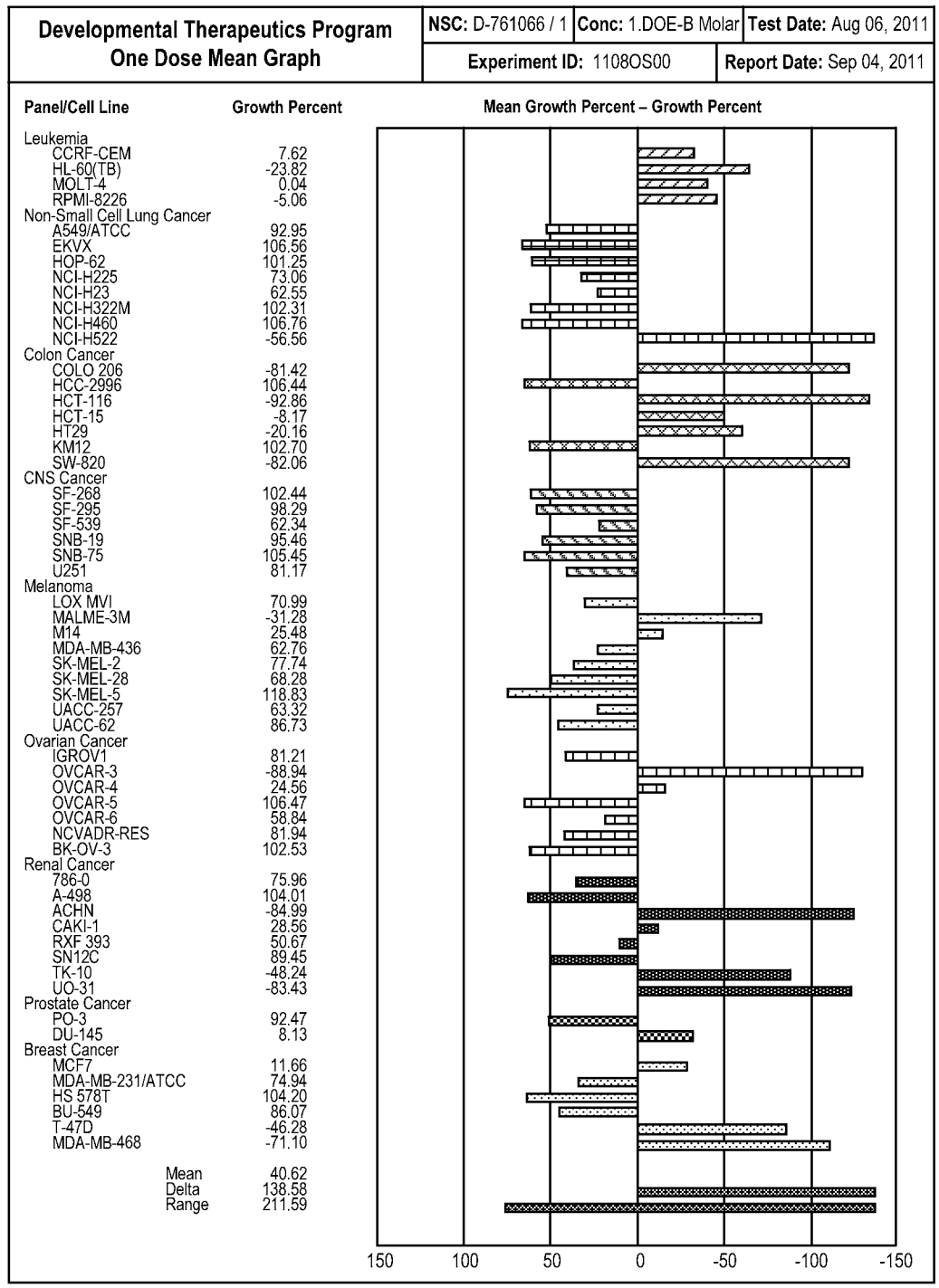
FIG. 7 shows results from the single dose screen conducted at NCI. The number reported for the One-dose assay is growth relative to the no-drug control, and relative to the time zero number of cells. Values between 0 and 100 indicates growth inhibition and values less than means lethality. For example, a value of 100 means no growth inhibition. A value of 40 would mean 60% growth inhibition. A value of 0 means no net growth over the course of the experiment. A value of −40 would mean 40% lethality. A value of −100 means all cells are dead.
Figure 8:
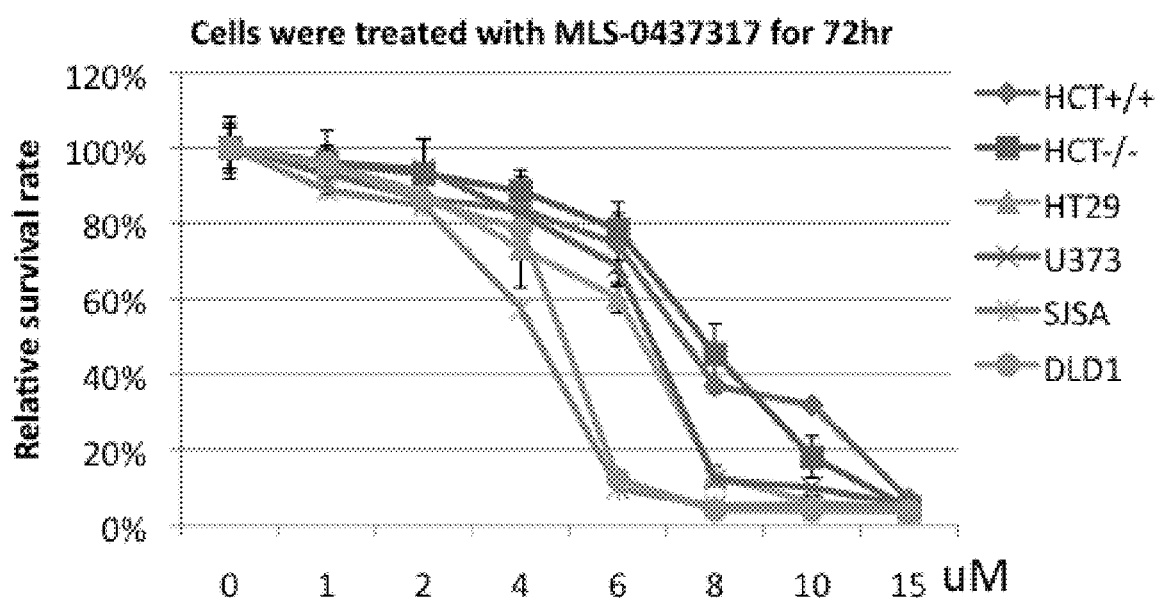
FIG. 8 illustrates the anticancer effects of E1 inhibitor MLS-0437317.
Figure 9:
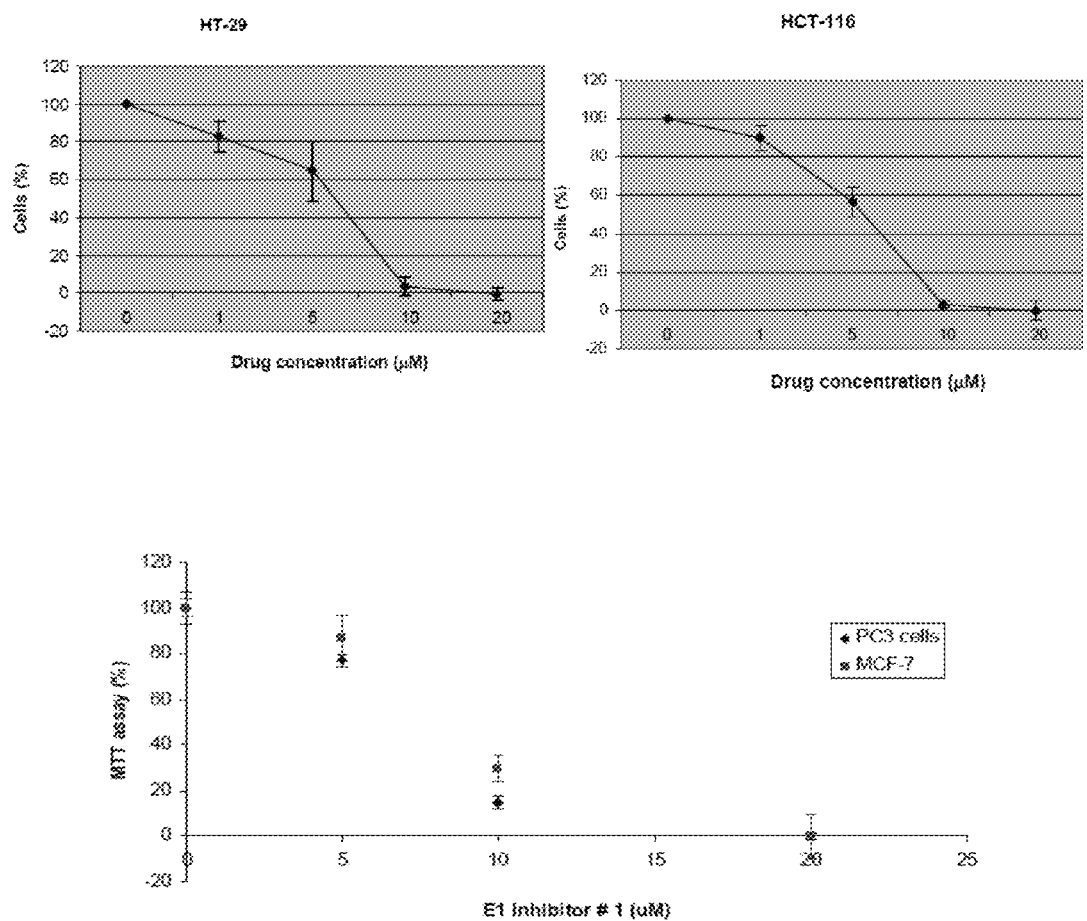
FIG. 9 illustrates cell viability of colorectal cancer cells (HT-29, HCT-115), pancreatic cells (PC3) and breast cancer cells (MCF7) treated with E1 inhibitor MLS-0437113 at various concentrations.

MLS-0437317 (Table 1 above) was also used to determine the dose response effect of an E1 inhibitor on cancer cells (FIG. 5), the anti-cancer effects of E1 inhibitors (MLS-0437113 and MLS-0437317) as measured by MTT assay on colorectal (HT-29, HT-116, DLD1), brain (U373), osteosarcoma (SJSA) pancreatic (PC3) and breast cancer cells (MCF-7) as shown in FIGS. 7-9.

Nanomolar Inhibitory Constant for the SUMO E1.

Figure 5:
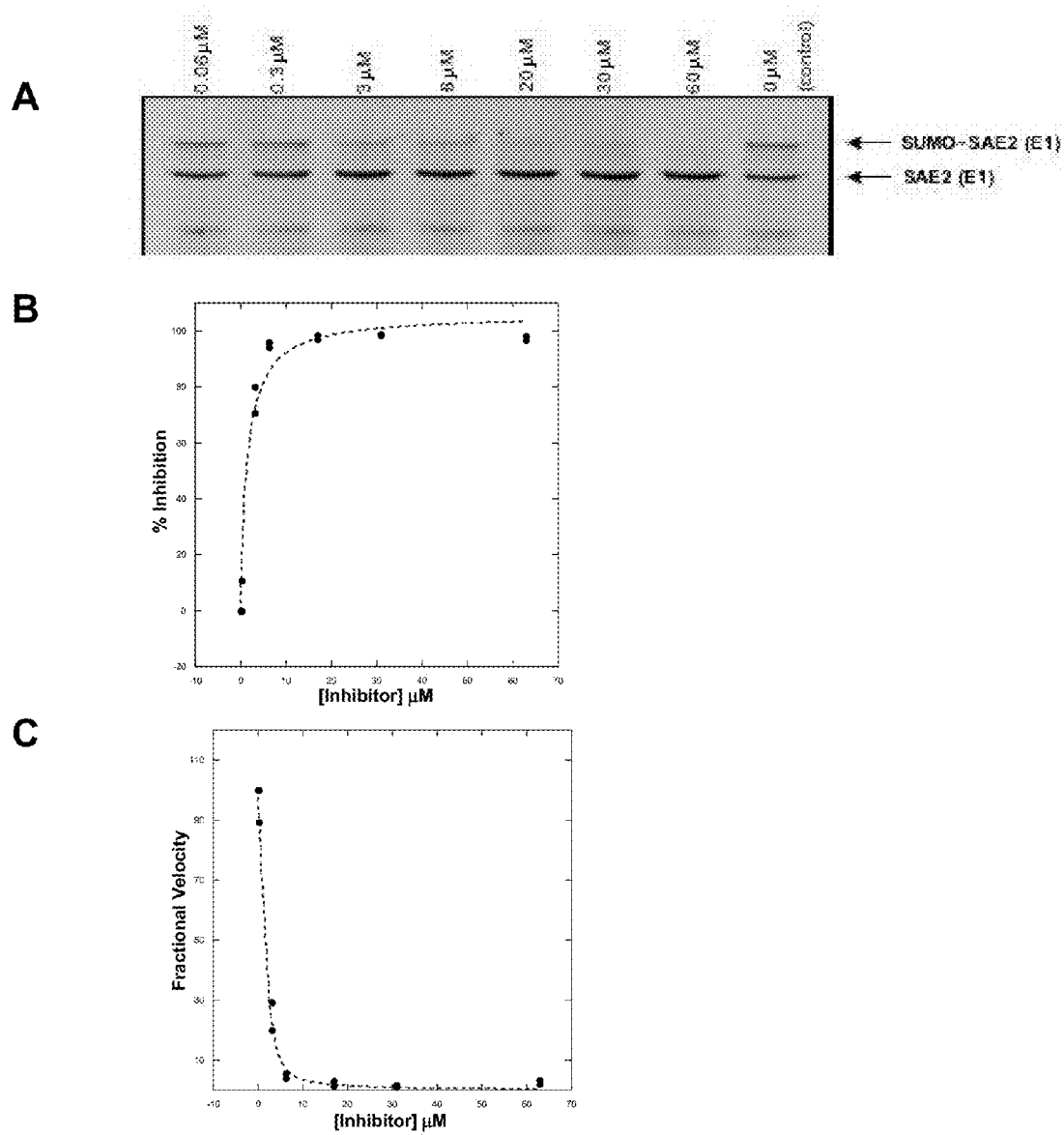
FIG. 5 shows a coomassie-stained gel of dose dependent SUMO~E1 inhibition (top) upon treatment with MLS-0437317. Data is analyzed by fitting to a rectangular hyperbolic to extract $IC_{50}$ (lower left) or the solution to a quadratic equation to determine $K_i^{app}$ (lower right).

Based on the structure-activity relationship (SAR) information obtained as summarized in FIG. 3, four additional analogues were made that displayed similar potency but improved stability in Tris buffer. Their inhibitory constants were measured in the reaction to monitor the rate of SUMO~E1 product formation in the presence of increasing concentrations of inhibitors (FIG. 5). Inhibition studies were performed in both the presence and absence of 0.02% Triton X-100 to ensure against potential promiscuous inhibition by premicelles due to the formation of aggregates. Inhibition data was fit to a rectangular hyperbolic to extract an IC$_{50}$ (Equation 1). The $K_i^{app}$ was extracted by fitting the percent inhibition as a function of inhibitor concentration using equations 1 and 2 (FIG. 5) (Spengler et al. 2005).

$$\% \text{ Inhibition} = ([I]*V_{max})/([I]+IC_{50}) \quad \text{(Equation 1)}$$

$$v/v_0 = (1-(([E]_0+[I]+K_i^{app})-(([E]_0+[I]+K_i^{app})^2 - 4([E]_0[I]))^{1/2})/2[E]_0 \quad \text{(Equation 2)}$$

MLS0437113 and several most potent analogues synthesized later displayed a submicromolar inhibition. Inhibition constants are displayed for representatives inhibitors families in Table 4 below.

TABLE 4

The apparent inhibitory constants for the SUMO E1 inhibitors. Selectivity of the inhibitors for the SUMO E1 versus the ubiquitin E1 is derived from the IC$_{50}$s of HTS assays.

| Compound number | Structure | SUMO E1 K$_i^{app}$ (mM) | SUMO/ubiquitin Selectivity |
|---|---|---|---|
| MLS-0437313 | 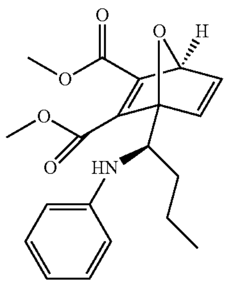 [SMILES: CCC[C@@H](Nc1ccccc1)C12C=C[C@H](O1)C(C(=O)OC)=C2C(=O)OC] | 0.26 ± 0.05 | >100 |
| MLS-0437317 | 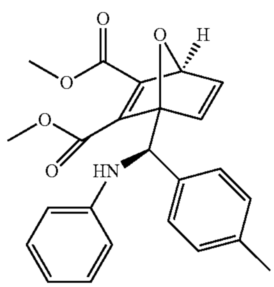 | 0.48 ± 0.21 | >100 |
| MLS-0437320 | 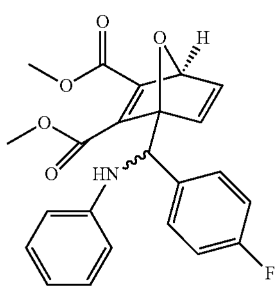 [SMILES: COC(=O)C1=C(C(=O)OC)C2(C(Nc3ccccc3)c3ccc(F)cc3)C=C[C@@H]1O2] | 4.2 ± 0.81 | >100 |
| MLS-0437321 | 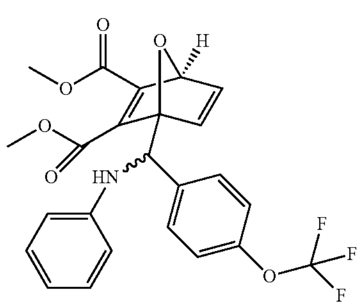 [SMILES: COC(=O)C1=C(C(=O)OC)C2(C(Nc3ccccc3)c3ccc(OC(F)(F)F)cc3)C=C[C@@H]1O2] | 0.82 ± 0.36 | >100 |

Stability of the Lead Compounds.

The original lead compound MLS-0437113 was found to be unstable in Tris buffer, and thus all compounds that displayed inhibitory activity at low μM range were tested for stability in Tris buffer. Stable compounds in Tris were tested with and without BSA. Amount of parent compound remaining was quantified using HPLC-MS (area under the curve (AUC) method). The results are summarized in Table 5.

TABLE 5

Stability of several compounds in Tris buffer

| Compound | % Remaining after 60 min in 50 mM Tris (−BSA) | % Remaining after 60 min in 50 mM Tris (+BSA) |
|---|---|---|
| MLS-0437113 | 0 | Not tested |
| MLS-0437120 | 29 | Not tested |

TABLE 5-continued

Stability of several compounds in Tris buffer

| Compound | % Remaining after 60 min in 50 mM Tris (−BSA) | % Remaining after 60 min in 50 mM Tris (+BSA) |
|---|---|---|
| MLS-0437313 | 48 | 89 |
| MLS-0437317 | 86 | 85 |
| MLS-0437319 | 36 | Not tested |
| MLS-0437320 | 84 | 87 |
| MLS-0437321 | 82 | 64 |

Because compound MLS-0437317 is stable as well as maintains high potency, some cellular studies were conducted on this compound, while others were conducted on the similarly potent MLS-0437113 in experiments where Tris buffer was not used.

Example 3

SUMO E1 Inhibitor Effects on Cancer Cells

Inhibition of SUMOylation in Cells.

Figure 6:
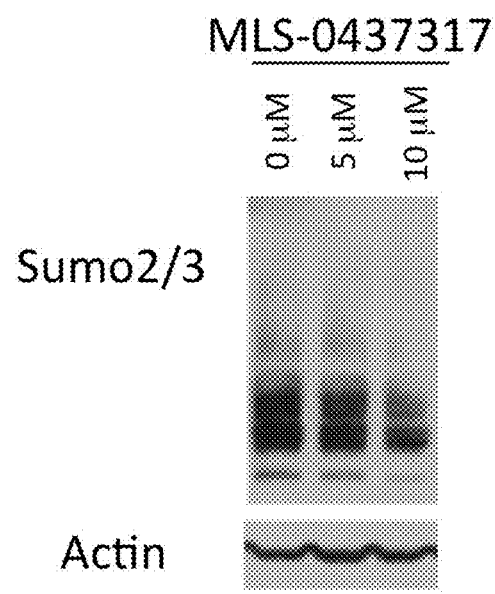
FIG. 6 shows MLS-0437317 inhibited global SUMOylation in a dose-dependent manner. Western blots (probed with anti-SUMO2/3 antibodies) of cell lysates from MCF-7 cells treated with the inhibitor. SUMO2/3 modifies many proteins as poly-SUMO chains, and is detected as high molecular weight smears.

The ability of MLS-0437317 to specifically inhibit SUMO E1 in cells by inhibition of global SUMOylation was investigated. In this experiment, the compound was added to cell culture media at the indicated concentrations for 8-18 h. Then SUMOylated proteins were detected using anti-SUMO antibodies. MLS-0437317 inhibited SUMOylation in a dose-dependent manner in MCF-7 cells (FIG. 6). Similar results were found in other cancer cell lines, including DLD1, H1299 and SJSA.

Inhibition of Growth as Well as Killing Specific Cancer Cell Lines.

MLS-0437317 was submitted to the In Vitro Cell Line Screening Project (IVCLSP) provided by the Developmental Therapeutics Program anticancer drug discovery program at National Cancer Institute. This screen uses 60 different human tumor cell lines, representing leukemia, melanoma and cancers of the lung, colon, brain, ovary, breast, prostate, and kidney. This screen is unique in that the complexity of a 60 cell line dose response produced by a given compound results in a biological response pattern which can be utilized in pattern recognition algorithms (COMPARE program. See: http://dtp.nci.nih.gov/docs/compare/compare.html). Using these algorithms, a putative mechanism of action may be assigned to a test compound, the response pattern may be determined to be unique and not similar to that of any of the standard prototype compounds included in the NCI database (see DTP Overview tab), or both. In addition, following characterization of various cellular molecular targets in the 60 cell lines, compounds that are most likely to interact with a specific molecular target may be identified and selected.

The screening is a two-stage process, beginning with the evaluation of all compounds against the 60 cell lines at a single dose of 10 uM. FIG. 7 shows the output from the single dose screen. The number reported for the One-dose assay is growth relative to the no-drug control, and relative to the time zero number of cells. This allows detection of both growth inhibition (values between 0 and 100) and lethality (values less than 0). For example, a value of 100 means no growth inhibition. A value of 40 would mean 60% growth inhibition. A value of 0 means no net growth over the course of the experiment. A value of −40 would mean 40% lethality. A value of −100 means all cells are dead.

Figure 10:
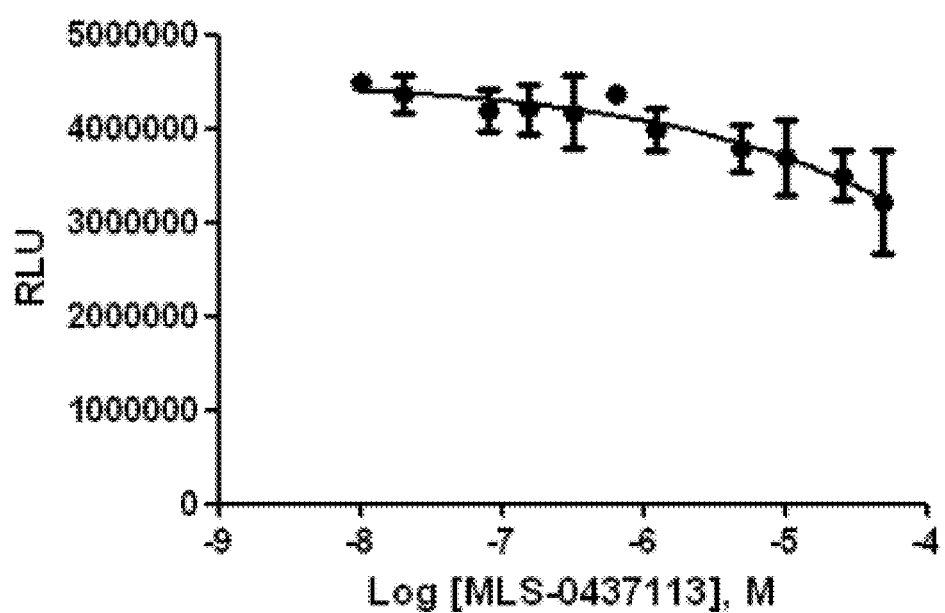
FIG. 10 illustrates that E1 inhibitor MLS-0437113 has low toxicity in a normal liver cell line. Immortalized human hepatocytes, Fa2N-4 cells (XenoTech) were seeded at ~50-60K cells/well, and incubated with a range of concentrations (0.01-50 µM) 1, in duplicate, for 24 hrs at 37° C., 5% CO2. Cell viability was determined by cellular ATP levels using the Luminescence ATP Detection Assay System (Tecan).

The compound exhibited selective toxicity toward certain cancer cell lines. Interestingly, it is effective for all Leukemia and most colorectal cancer cell lines. In addition, it is effective for at least one of the cell lines of all cancer types in this panel, indicating that the SUMO E1 inhibitors described herein may have a broad applicability to many types of cancer. This compound may be tested using five concentration levels, to determine its most effective dose or minimally effective dose. The selective toxicity is consistent with low toxicity in immortalized human hepatocytes Fa2N-4, which is a control for normal cells, and no toxicity was detected with concentrations up to 50 μM (FIG. 10).

The screening methodology is described as follows (see http://dtp.nci.nih.gov/). The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs. After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA).

Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$$[(Ti-Tz)/(C-Tz)] \times 100 \text{ for concentrations for which } Ti >/= Tz$$

$$[(Ti-Tz)/Tz] \times 100 \text{ for concentrations for which } Ti < Tz.$$

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]× 100=−50. Values are calculated for each of these three parameters if the level of activity is reached; however, if the effect is not reached or is exceeded, the value for that parameter is expressed as greater or less than the maximum or minimum concentration tested.

Sensitization of Cancer Cells to DNA-Damaging Radiation.

It was tested whether a potent compound from this series could sensitize cancer cells to genotoxic stress. The inhibitor was added to cultures of various cancer cell lines for 30 minutes to 1 d, after which cells were irradiated at 4 Gy. Forty-eight hours after irradiation, cell viability was measured by an MTS assay. Addition of the inhibitor significantly enhanced the sensitivity of tested cancer cell lines to radiation (FIG. 11; only representative lines are shown due to space limitations).

REFERENCES al-Khodairy, F., Enoch, T., Hagan, I. M., and Carr, A. M. (1995) *J Cell Sci* 108 (Pt 2), 475-486

Andrews, E. A., Palecek, J., Sergeant, J., Taylor, E., Lehmann, A. R., and Watts, F. Z. (2005) *Mol Cell Biol* 25, 185-196

Bartek, J. and Z. Hodny, SUMO boosts the DNA damage response barrier against cancer. *Cancer Cell*, 2010. 17(1): p. 9-11.

Bartek, J. and Z. Hodny, SUMO boosts the DNA damage response barrier against cancer. *Cancer Cell*, 2010. 17(1): p. 9-11.

Bergink, S, and S. Jentsch, Principles of ubiquitin and SUMO modifications in DNA repair. *Nature*, 2009. 458(7237): p. 461-7.

Boggio, R. and S. Chiocca, Viruses and sumoylation: recent highlights. *Curr Opin Microbiol*, 2006. 9(4): p. 430-6.

Bohnsack, R. N. and A. L. Haas, Conservation in the mechanism of Nedd8 activation by the human AppBp1-Uba3 heterodimer. *J Biol Chem*, 2003. 278(29): p. 26823-30.

Burgess, R. C., Rahman, S., Lisby, M., Rothstein, R., and Zhao, X. (2007) *Molecular and cellular biology* 27, 6153-6162

Burt, C. G., R. R. Cima, W. A. Koltun, C. E. Littlejohn, R. Ricciardi, L. K. Temple, D. A. Rothenberger, and N. N. Baxter, Developing a research agenda for the American Society of Colon and Rectal Surgeons: results of a delphi approach. *Dis Colon Rectum*, 2009. 52(5): p. 898-905.

Cano, K. E., Y. J. Li, and Y. Chen, NMR metabolomic profiling reveals new roles of SUMOylation in DNA damage response. *J Proteome Res*, 2010. 9(10): p. 5382-8.

Cao, X., C. Clavijo, X. Li, H. H. Lin, Y. Chen, H. M. Shih, and D. K. Ann, SUMOylation of HMGA2: selective destabilization of promyelocytic leukemia protein via proteasome. *Mol Cancer Ther*, 2008. 7(4): p. 923-34.

Carter, S., O. Bischof, A. Dejean, and K. H. Vousden, C-terminal modifications regulate MDM2 dissociation and nuclear export of p53. *Nat Cell Biol*, 2007. 9(4): p. 428-35.

Chekmarev, D. S., S. V. Shorshnev, A. E. Stepanov, A. N. Kasatkin, Highly selective substitutions in 2,3-dichloropyrazine. A novel general approach to aloisines. *Tetrahedron*, 2006, 62, 9919-9930.

Chen, Y., The enzymes in ubiquitin-like post-translational modifications. *Biosci Trends*, 2007. 1(1): p. 16-25.

Cheng, J., X. Kang, S. Zhang, and E. T. Yeh, SUMO-specific protease 1 is essential for stabilization of HIF1alpha during hypoxia. *Cell*, 2007. 131(3): p. 584-95.

Chung, V., B. Zhou, X. Liu, L. Zhu, L. M. Boo, H. V. Nguyen, D. K. Ann, J. Song, Y. Chen, and Y. Yen, SUMOylation plays a role in gemcitabine- and bortezomib-induced cytotoxicity in human oropharyngeal carcinoma KB gemcitabine-resistant clone. *Mol Cancer Ther*, 2006. 5(3): p. 533-40.

Comerford, K. M., M. O. Leonard, J. Karhausen, R. Carey, S. P. Colgan, and C. T. Taylor, Small ubiquitin-related modifier-1 modification mediates resolution of CREB-dependent responses to hypoxia. *Proc Natl Acad Sci USA*, 2003. 100(3): p. 986-91.

Cook, C. E., Hochstrasser, M., and Kerscher, O. (2009) *Cell Cycle* 8, 1080-1089

Darzynkiewicz, Z., F. Traganos, and D. Wlodkowic, Impaired DNA damage response—an Achilles' heel sensitizing cancer to chemotherapy and radiotherapy. *Eur J Pharmacol*, 2009. 625(1-3): p. 143-50.

de Vries, S. J., M. van Dijk, and A. M. Bonvin, The HADDOCK web server for data-driven biomolecular docking. *Nat Protoc*, 2010. 5(5): p. 883-97.

Doksani, Y., R. Bermejo, S. Fiorani, J. E. Haber, and M. Foiani, Replicon dynamics, dormant origin firing, and terminal fork integrity after double-strand break formation. *Cell*, 2009. 137(2): p. 247-58.

Doksani, Y., R. Bermejo, S. Fiorani, J. E. Haber, and M. Foiani, Replicon dynamics, dormant origin firing, and terminal fork integrity after double-strand break formation. *Cell*, 2009. 137(2): p. 247-58.

Dominguez, C., R. Boelens, and A. M. Bonvin, HADDOCK: a protein-protein docking approach based on biochemical or biophysical information. *J Am Chem Soc*, 2003. 125(7): p. 1731-7.

Driscoll, J. J. and R. Dechowdhury, Therapeutically targeting the SUMOylation, Ubiquitination and Proteasome pathways as a novel anticancer strategy. *Target Oncol*, 2010. 5(4): p. 281-9.

Fukui, L. and Y. Chen, NvMap: automated analysis of NMR chemical shift perturbation data. *Bioinformatics*, 2007. 23(3): p. 378-80.

Galanty, Y., R. Belotserkovskaya, J. Coates, S. Polo, K. M. Miller, and S. P. Jackson, Mammalian SUMO E3-ligases PIAS1 and PIAS4 promote responses to DNA double-strand breaks. *Nature*, 2009. 462(7275): p. 935-9.

Galanty, Y., R. Belotserkovskaya, J. Coates, S. Polo, K. M. Miller, and S. P. Jackson, Mammalian SUMO E3-ligases PIAS1 and PIAS4 promote responses to DNA double-strand breaks. *Nature*, 2009. 462(7275): p. 935-9.

Garcia-Aguilar, J., E. Hernandez de And a, P. Sirivongs, S. H. Lee, R. D. Madoff, and D. A. Rothenberger, A pathologic complete response to preoperative chemoradiation is associated with lower local recurrence and improved survival in rectal cancer patients treated by mesorectal excision. *Dis Colon Rectum*, 2003. 46(3): p. 298-304.

Genin, E., M. Reboud-Ravaux, and J. Vidal, Proteasome inhibitors: recent advances and new perspectives in medicinal chemistry. *Curr Top Med. Chem.* 10(3): p. 232-56.

Genin, E., M. Reboud-Ravaux, and J. Vidal, Proteasome inhibitors: recent advances and new perspectives in medicinal chemistry. *Curr Top Med. Chem.* 10(3): p. 232-56.

Gilbreth, R. N., K. Truong, I. Madu, A. Koide, J. Wojcik, N.-S. Li, J. A. Piccirilli, Y. Chen, and S. Koide, Isoform-specific Monobody Inhibitors of SUMO/SIM Interactions Engineered Using Structure-guided Library Design. *Proceedings of the National Academy of Sciences*, 2011. in press.

Gostissa, M., A. Hengstermann, V. Fogal, P. Sandy, S. E. Schwarz, M. Scheffner, and G. Del Sal, Activation of p53 by conjugation to the ubiquitin-like protein SUMO-1. *Embo J*, 1999. 18(22): p. 6462-71.

Haas, A. L. and I. A. Rose, The mechanism of ubiquitin activating enzyme. A kinetic and equilibrium analysis. *J Biol Chem*, 1982. 257(17): p. 10329-37.

Hay, R. T., SUMO: a history of modification. *Mol Cell*, 2005. 18(1): p. 1-12.

Hay, R. T., SUMO: a history of modification. *Mol Cell*, 2005. 18(1): p. 1-12.

Huang, D. T., H. W. Hunt, M. Zhuang, M. D. Ohi, J. M. Holton, and B. A. Schulman, Basis for a ubiquitin-like protein thioester switch toggling E1-E2 affinity. *Nature*, 2007. 445(7126): p. 394-8.

Ii, T., Mullen, J. R., Slagle, C. E., and Brill, S. J. (2007) *DNA Repair (Amst)* 6, 1679-1691

Jaber, T., C. R. Bohl, G. L. Lewis, C. Wood, J. T. West, Jr., and R. A. Weldon, Jr., Human Ubc9 contributes to production of fully infectious human immunodeficiency virus type 1 virions. *J Virol*, 2009. 83(20): p. 10448-59.

Jeggo, P. and M. F. Lavin, Cellular radiosensitivity: how much better do we understand it? *Int J Radiat Biol*, 2009. 85(12): p. 1061-81.

Keshelava, N., T. Frgala, J. Krejsa, O. Kalous, and C. P. Reynolds, DIMSCAN: a microcomputer fluorescence-based cytotoxicity assay for preclinical testing of combination chemotherapy. *Methods Mol Med*, 2005. 110: p. 139-53.

Kho, C., A. Lee, D. Jeong, J. G. Oh, A. H. Chaanine, E. Kizana, W. J. Park, and R. J. Hajjar, SUMO1-dependent modulation of SERCA2a in heart failure. *Nature*, 2011. 477(7366): p. 601-5.

Kim, J. H., H. J. Choi, B. Kim, M. H. Kim, J. M. Lee, I. S. Kim, M. H. Lee, S. J. Choi, K. I. Kim, S. I. Kim, C. H. Chung, and S. H. Baek, Roles of sumoylation of a reptin chromatin-remodelling complex in cancer metastasis. *Nat Cell Biol*, 2006. 8(6): p. 631-9.

Kim, E. T., Y. E. Kim, Y. H. Huh, and J. H. Ahn, Role of noncovalent SUMO binding by the human cytomegalovirus 1E2 transactivator in lytic growth. *J. Virol*. 84(16): p. 8111-23.

Kim, K. I. and S. H. Baek, SUMOylation code in cancer development and metastasis. *Mol Cells*, 2006. 22(3): p. 247-53.

Li, Y. J., J. M. Stark, D. J. Chen, D. K. Ann, and Y. Chen, Role of SUMO:SIM-mediated protein-protein interaction in non-homologous end joining. *Oncogene*, 2010. 29(24): p. 3509-18.

Li, Y. J., J. M. Stark, D. J. Chen, D. K. Ann, and Y. Chen, Role of SUMO:SIM-mediated protein-protein interaction in non-homologous end joining. *Oncogene*, 2010. 29(24): p. 3509-18.

Li, T., R. Santockyte, R. F. Shen, E. Tekle, G. Wang, D. C. Yang, and P. B. Chock, Expression of SUMO-2/3 induced senescence through p53- and pRB-mediated pathways. *J Biol Chem*, 2006. 281(47): p. 36221-7.

Lin, D., M. H. Tatham, B. Yu, S. Kim, R. T. Hay, and Y. Chen, Identification of a substrate recognition site on Ubc9. *J Biol Chem*, 2002. 277(24): p. 21740-8.

Liu, Q., C. Jin, X. Liao, Z. Shen, D. J. Chen, and Y. Chen, The binding interface between an E2 (UBC9) and a ubiquitin homologue (UBL1). *J Biol Chem*, 1999. 274(24): p. 16979-87.

Liu, Q., Y. C. Yuan, B. Shen, D. J. Chen, and Y. Chen, Conformational flexibility of a ubiquitin conjugation enzyme (E2). *Biochemistry*, 1999. 38(5): p. 1415-25.

Liu, Q., B. Shen, D. J. Chen, and Y. Chen, Backbone resonance assignments of human UBC9. *J Biomol NMR*, 1999. 13(1): p. 89-90.

Liu, B., S. Tahk, K. M. Yee, G. Fan, and K. Shuai, The ligase PIAS1 restricts natural regulatory T cell differentiation by epigenetic repression. *Science*, 2010. 330(6003): p. 521-5.

Lois, L. M. and C. D. Lima, Structures of the SUMO E1 provide mechanistic insights into SUMO activation and E2 recruitment to E1. *Embo J*, 2005. 24(3): p. 439-51.

Luo, J., M. J. Emanuele, D. Li, C. J. Creighton, M. R. Schlabach, T. F. Westbrook, K. K. Wong, and S. J. Elledge, A genome-wide RNAi screen identifies multiple synthetic lethal interactions with the Ras oncogene. *Cell*, 2009. 137(5): p. 835-48.

Luo, J., M. J. Emanuele, D. Li, C. J. Creighton, M. R. Schlabach, T. F. Westbrook, K. K. Wong, and S. J. Elledge, A genome-wide RNAi screen identifies multiple synthetic lethal interactions with the Ras oncogene. *Cell*, 2009. 137(5): p. 835-48.

Martin, S., K. A. Wilkinson, A. Nishimune, and J. M. Henley, Emerging extranuclear roles of protein SUMOylation in neuronal function and dysfunction. *Nat Rev Neurosci*, 2007. 8(12): p. 948-59.

Mayer, M. and B. Meyer, Group epitope mapping by saturation transfer difference NMR to identify segments of a ligand in direct contact with a protein receptor. *J Am Chem Soc*, 2001. 123(25): p. 6108-17.

Mo, Y. Y. and S. J. Moschos, Targeting Ubc9 for cancer therapy. *Expert Opin Ther Targets*, 2005. 9(6): p. 1203-16.

Mo, Y. Y. and S. J. Moschos, Targeting Ubc9 for cancer therapy. *Expert Opin Ther Targets*, 2005. 9(6): p. 1203-16.

Mo, Y. Y., Y. Yu, E. Theodosiou, P. L. Ee, and W. T. Beck, A role for Ubc9 in tumorigenesis. *Oncogene*, 2005. 24(16): p. 2677-83.

Mohan, R. D., A. Rao, J. Gagliardi, and M. Tini, SUMO-1-dependent allosteric regulation of thymine DNA glycosylase alters subnuclear localization and CBP/p300 recruitment. *Mol Cell Biol*, 2007. 27(1): p. 229-43.

Mohan, R. D., A. Rao, J. Gagliardi, and M. Tini, SUMO-1-dependent allosteric regulation of thymine DNA glycosylase alters subnuclear localization and CBP/p300 recruitment. *Mol Cell Biol*, 2007. 27(1): p. 229-43.

Morris, J. R., C. Boutell, M. Keppler, R. Densham, D. Weekes, A. Alamshah, L. Butler, Y. Galanty, L. Pangon, T. Kiuchi, T. Ng, and E. Solomon, The SUMO modification pathway is involved in the BRCA1 response to genotoxic stress. *Nature*, 2009. 462(7275): p. 886-90.

Morris, J. R., C. Boutell, M. Keppler, R. Densham, D. Weekes, A. Alamshah, L. Butler, Y. Galanty, L. Pangon, T. Kiuchi, T. Ng, and E. Solomon, The SUMO modification pathway is involved in the BRCA1 response to genotoxic stress. *Nature*, 2009. 462(7275): p. 886-90.

Muller, S., M. Berger, F. Lehembre, J. S. Seeler, Y. Haupt, and A. Dejean, c-Jun and p53 activity is modulated by SUMO-1 modification. *J Biol Chem*, 2000. 275(18): p. 13321-9.

Nagai, S., Dubrana, K., Tsai-Pflugfelder, M., Davidson, M. B., Roberts, T. M., Brown, G. W., Varela, E., Hediger, F., Gasser, S. M., and Krogan, N. J. (2008) *Science* (New York, N.Y. 322, 597-602

Nguyen, H. V., J. L. Chen, J. Zhong, K. J. Kim, E. D. Crandall, Z. Borok, Y. Chen, and D. K. Ann, SUMOylation attenuates sensitivity toward hypoxia- or desferroxamine-induced injury by modulating adaptive responses in salivary epithelial cells. *Am J Pathol,* 2006. 168(5): p. 1452-63.

Ohmori, J., M. Shimizu-Sasamata, M. Okada, S. Sakamoto, 8-(1*H*-*Imidazol*-1-*yl*)-7-*nitro*-4(5*H*)*imidazo[1,2-a]quinoxalinone and Related Compounds: Synthesis and Structure Activity Relationships for the AMPA-type Non-NMDA Receptor. J. Med. Chem.* 1997, 40, 2053-2063.

Olsen, S. K., A. D. Capili, X. Lu, D. S. Tan, and C. D. Lima, Active site remodelling accompanies thioester bond formation in the SUMO E1. *Nature.* 463(7283): p. 906-12.

Ouyang, K. J., L. L. Woo, J. Zhu, D. Huo, M. J. Matunis, and N. A. Ellis, SUMO modification regulates BLM and RAD51 interaction at damaged replication forks. *PLoS Biol,* 2009. 7(12): p. e1000252.

Pellecchia, M., D. Meininger, Q. Dong, E. Chang, R. Jack, and D. S. Sem, NMR-based structural characterization of large protein-ligand interactions. *J Biomol NMR,* 2002. 22(2): p. 165-73.

Pfander, B., G. L. Moldovan, M. Sacher, C. Hoege, and S. Jentsch, SUMO-modified PCNA recruits Srs2 to prevent recombination during S phase. *Nature,* 2005. 436(7049): p. 428-33.

Pfander, B., G. L. Moldovan, M. Sacher, C. Hoege, and S. Jentsch, SUMO-modified PCNA recruits Srs2 to prevent recombination during S phase. *Nature,* 2005. 436(7049): p. 428-33.

Prudden, J., Pebernard, S., Raffa, G., Slavin, D. A., Perry, J. J., Tainer, J. A., McGowan, C. H., and Boddy, M. N. (2007) *Embo J* 26, 4089-4101

Prudden, J., J. J. Perry, A. S. Arvai, J. A. Tainer, and M. N. Boddy, Molecular mimicry of SUMO promotes DNA repair. *Nat Struct Mol Biol,* 2009. 16(5): p. 509-16.

Reibarkh, M., T. J. Malia, and G. Wagner, NMR distinction of single- and multiple-mode binding of small-molecule protein ligands. *J Am Chem Soc,* 2006. 128(7): p. 2160-1.

Religa, T. L. and L. E. Kay, Optimal methyl labeling for studies of supra-molecular systems. *J Biomol NMR.* 47(3): p. 163-9.

Ribet, D., M. Hamon, E. Gouin, M. A. Nahori, F. Impens, H. Neyret-Kahn, K. Gevaert, J. Vandekerckhove, A. Dejean, and P. Cossart, *Listeria monocytogenes* impairs SUMOylation for efficient infection. *Nature,* 2010. 464(7292): p. 1192-5.

Ribet, D., M. Hamon, E. Gouin, M. A. Nahori, F. Impens, H. Neyret-Kahn, K. Gevaert, J. Vandekerckhove, A. Dejean, and P. Cossart, *Listeria monocytogenes* impairs SUMOylation for efficient infection. *Nature,* 2010. 464(7292): p. 1192-5.

Rouleau, N., J. Wang, L. Karras, E. Andrews, M. Bielefeld-Sevigny, and Y. Chen, Highly sensitive assays for SUMOylation and small ubiquitin-like modifier-dependent protein-protein interactions. *Anal Biochem,* 2008. 375(2): p. 364-6.

Sarge, K. D. and O. K. Park-Sarge, Sumoylation and human disease pathogenesis. *Trends Biochem Sci,* 2009. 34(4): p. 200-5.

Sarge, K. D. and O. K. Park-Sarge, Sumoylation and human disease pathogenesis. *Trends Biochem Sci,* 2009. 34(4): p. 200-5.

Sarge, K. D. and O. K. Park-Sarge, SUMO and its role in human diseases. *Int Rev Cell Mol Biol,* 2011. 288: p. 167-83.

Seu, C. S, and Y. Chen, Identification of SUMO-binding motifs by NMR. *Methods Mol Biol,* 2009. 497: p. 121-38.

Shayeghi, M., Doe, C. L., Tavassoli, M., and Watts, F. Z. (1997) *Nucleic Acids Res* 25, 1162-1169

Song, J., L. K. Durrin, T. A. Wilkinson, T. G. Krontiris, and Y. Chen, Identification of a SUMO-binding motif that recognizes SUMO-modified proteins. *Proc Natl Acad Sci USA,* 2004. 101(40): p. 14373-8.

Song, J., L. K. Durrin, T. A. Wilkinson, T. G. Krontiris, and Y. Chen, Identification of a SUMO-binding motif that recognizes SUMO-modified proteins. *Proc Natl Acad Sci USA,* 2004. 101(40): p. 14373-8.

Song, J., Z. Zhang, W. Hu, and Y. Chen, Small ubiquitin-like modifier (SUMO) recognition of a SUMO binding motif: a reversal of the bound orientation. *J Biol Chem,* 2005. 280 (48): p. 40122-9.

Song, J., Z. Zhang, W. Hu, and Y. Chen, Small ubiquitin-like modifier (SUMO) recognition of a SUMO binding motif: a reversal of the bound orientation. *J Biol Chem,* 2005. 280 (48): p. 40122-9.

Song, J., J. Wang, A. A. Jozwiak, W. Hu, P. M. Swiderski, and Y. Chen, Stability of thioester intermediates in ubiquitin-like modifications. *Protein Sci,* 2009. 18(12): p. 2492-9.

Sprangers, R., A. Velyvis, and L. E. Kay, Solution NMR of supramolecular complexes: providing new insights into function. *Nat Methods,* 2007. 4(9): p. 697-703.

Spengler, M. L., S. B. Kennett, K. S. Moorefield, S. O. Simmons, M. G. Brattain, and J. M. Horowitz, Sumoylation of internally initiated Sp3 isoforms regulates transcriptional repression via a Trichostatin A-insensitive mechanism. *Cell Signal,* 2005. 17(2): p. 153-66.

Steffan, J. S., N. Agrawal, J. Pallos, E. Rockabrand, L. C. Trotman, N. Slepko, K. Illes, T. Lukacsovich, Y. Z. Zhu, E. Cattaneo, P. P. Pandolfi, L. M. Thompson, and J. L. Marsh, SUMO modification of Huntingtin and Huntington's disease pathology. *Science,* 2004. 304(5667): p. 100-4.

Steffan, J. S., N. Agrawal, J. Pallos, E. Rockabrand, L. C. Trotman, N. Slepko, K. Illes, T. Lukacsovich, Y. Z. Zhu, E. Cattaneo, P. P. Pandolfi, L. M. Thompson, and J. L. Marsh, SUMO modification of Huntingtin and Huntington's disease pathology. *Science,* 2004. 304(5667): p. 100-4.

Stehmeier, P. and S. Muller, Regulation of p53 family members by the ubiquitin-like SUMO system. *DNA Repair (Amst),* 2009. 8(4): p. 491-8.

Steinacher, R. and P. Schar, Functionality of human thymine DNA glycosylase requires SUMO-regulated changes in protein conformation. *Curr Biol,* 2005. 15(7): p. 616-23.

Steinacher, R. and P. Schar, Functionality of human thymine DNA glycosylase requires SUMO-regulated changes in protein conformation. *Curr Biol,* 2005. 15(7): p. 616-23.

Subramaniam, S., K. M. Sixt, R. Barrow, and S. H. Snyder, Rhes, a striatal specific protein, mediates mutant-huntingtin cytotoxicity. *Science,* 2009. 324(5932): p. 1327-30.

Subramaniam, S., K. M. Sixt, R. Barrow, and S. H. Snyder, Rhes, a striatal specific protein, mediates mutant-huntingtin cytotoxicity. *Science,* 2009. 324(5932): p. 1327-30.

Sun, H., Leverson, J. D., and Hunter, T. (2007) *Embo J* 26, 4102-4112

Tan, J. A., J. Song, Y. Chen, and L. K. Durrin, Phosphorylation-dependent interaction of SATB1 and PIAS1 directs SUMO-regulated caspase cleavage of SATB1. *Mol Cell Biol,* 2010. 30(11): p. 2823-36.

Tan, J. A., Y. Sun, J. Song, Y. Chen, T. G. Krontiris, and L. K. Durrin, SUMO conjugation to the matrix attachment region-binding protein, special AT-rich sequence-binding protein-1 (SATB1), targets SATB1 to promyelocytic nuclear bodies where it undergoes caspase cleavage. *J Biol Chem,* 2008. 283(26): p. 18124-34.

Tatham, M. H., S. Kim, E. Jaffray, J. Song, Y. Chen, and R. T. Hay, Unique binding interactions among Ubc9, SUMO and RanBP2 reveal a mechanism for SUMO paralog selection. *Nat Struct Mol Biol,* 2005. 12(1): p. 67-74.

Tatham, M. H., Y. Chen, and R. T. Hay, Role of two residues proximal to the active site of Ubc9 in substrate recognition by the Ubc9.SUMO-1 thiolester complex. *Biochemistry,* 2003. 42(11): p. 3168-79.

Tatham, M. H., S. Kim, B. Yu, E. Jaffray, J. Song, J. Zheng, M. S. Rodriguez, R. T. Hay, and Y. Chen, Role of an N-terminal site of Ubc9 in SUMO-1, -2, and -3 binding and conjugation. *Biochemistry,* 2003. 42(33): p. 9959-69.

Tatham, M. H., S. Kim, B. Yu, E. Jaffray, J. Song, J. Zheng, M. S. Rodriguez, R. T. Hay, and Y. Chen, Role of an N-terminal site of Ubc9 in SUMO-1, -2, and -3 binding and conjugation. *Biochemistry,* 2003. 42(33): p. 9959-69.

Tatham, M. H., B. Yu, S. Kim, E. Jaffray, M. S. Rodriguez, R. T. Hay, and Y. Chen, Identification of the initial docking site of the SUMO-1 moiety of the E1-SUMO-1 thiolester on E2. submitted., 2002.

Tokgoz, Z., R. N. Bohnsack, and A. L. Haas, Pleiotropic effects of ATP.Mg2+ binding in the catalytic cycle of ubiquitin-activating enzyme. *J Biol Chem,* 2006. 281(21): p. 14729-37.

Truong, K., Y. Su, J. Song, and Y. Chen, Entropy-Driven Mechanism of a SUMO Ligase. *Biochemistry,* 2011. in press.

Tugarinov, V., R. Sprangers, and L. E. Kay, Line narrowing in methyl-TROSY using zero-quantum 1H-13C NMR spectroscopy. *J Am Chem Soc,* 2004. 126(15): p. 4921-5.

Ulrich, H. D., Preface. Ubiquitin, SUMO and the maintenance of genome stability. *DNA Repair (Amst),* 2009. 8(4): p. 429.

Ulrich, H. D., The SUMO system: an overview. *Methods Mol Biol,* 2009. 497: p. 3-16.

van Attikum, H. and S. M. Gasser, Crosstalk between histone modifications during the DNA damage response. *Trends Cell Biol,* 2009. 19(5): p. 207-17.

van Dijk, A. D., S. J. de Vries, C. Dominguez, H. Chen, H. X. Zhou, and A. M. Bonvin, Data-driven docking: HADDOCK's adventures in CAPRI. *Proteins,* 2005. 60(2): p. 232-8.

Wang, J., B. Lee, S. Cai, L. Fukui, W. Hu, and Y. Chen, Conformational transition associated with E1-E2 interaction in small ubiquitin-like modifications. *J Biol Chem,* 2009. 284(30): p. 20340-8.

Wang, J., W. Hu, S. Cai, B. Lee, J. Song, and Y. Chen, The intrinsic affinity between E2 and the Cys domain of E1 in ubiquitin-like modifications. *Mol Cell,* 2007. 27(2): p. 228-37.

Wang, J., S. Cai, and Y. Chen, Mechanism of E1-E2 interaction for the inhibition of Ubl adenylation. *J Biol Chem,* 2010. 285(43): p. 33457-62.

Wang, J. and Y. Chen, Role of the Zn(2+) motif of E1 in SUMO adenylation. *J Biol Chem,* 2010. 285(31): p. 23732-8.

Wang, J., S. Cai, and Y. Chen, Mechanism of E1-E2 interaction for the inhibition of Ubl adenylation. *J Biol. Chem.*

Wang, J. and Y. Chen, Role of the Zn(2+) motif of E1 in SUMO adenylation. *J Biol Chem.* 285(31): p. 23732-8.

Wang, L. and S. Banerjee, Differential PIAS3 expression in human malignancy. *Oncol Rep,* 2004. 11(6): p. 1319-24.

Watanabe, T., Chemoradiation and adjuvant chemotherapy for rectal cancer. *Int J Clin Oncol,* 2008. 13: p. 488-97.

Wu, F. and Y. Y. Mo, Ubiquitin-like protein modifications in prostate and breast cancer. *Front Biosci,* 2007. 12: p. 700-11.

Yeh, E. T., SUMOylation and De-SUMOylation: wrestling with life's processes. *J Biol Chem,* 2009. 284(13): p. 8223-7.

Yeh, E. T., SUMOylation and De-SUMOylation: wrestling with life's processes. *J Biol Chem,* 2009. 284(13): p. 8223-7.

Zhao, X., and Blobel, G. (2005) *Proc Natl Acad Sci USA*

Zhu, S., M. Sachdeva, F. Wu, Z. Lu, and Y. Y. Mo, Ubc9 promotes breast cell invasion and metastasis in a sumoylation-independent manner. *Oncogene,* 2010. 29(12): p. 1763-72.

What is claimed is:

1. A SUMOylation inhibitor compound comprising the structure (i)

Or a pharmaceutically acceptable solvate, salt and stereoisomer thereof, including mixtures thereof in all ratios, wherein:

A is O, S, $NR_7$ where $R_7$ is H, alkyl, haloalkyl, alcoxyalkyl, aryl, heteroaryl, cycloalkyl, heterocyclyl, benzyl, alkyl-aryl where $R_7$ is optionally substituted with one to four $R_8$ groups, $CH_2$, $CH_2CH_2$, CH=CH;

B is O, S, $NR_{11}$ where $R_{11}$ is H, alkyl, haloalkyl, alcoxyalkyl, aryl, heteroaryl, cycloalkyl, heterocyclyl, benzyl, alkyl-aryl where $R_{11}$ is optionally substituted with one to four $R_8$ groups;

$R_1$ is H, alkyl, haloalkyl, alcoxyalkyl, aryl, heterocyclyl, heteroaryl, cycloalkyl, benzyl, alkyl-aryl where $R_1$ is optionally substituted with one to four $R_8$ groups;

$R_2$ is H, alkyl, haloalkyl, alcoxyalkyl, aryl, heterocyclyl, heteroaryl, cycloalkyl, benzyl, alkyl-aryl where $R_2$ is optionally substituted with one to four $R_8$ groups;

$R_3$ is —C(O)—$OR_9$, ON, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;

$R_4$ is —C(O)—$OR_9$, ON, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;

$R_5$ is H, alkyl, haloalkyl, alcoxyalkyl, aryl, heterocyclyl, heteroaryl, cycloalkyl, benzyl, alkyl-aryl where $R_5$ is optionally substituted with one to four $R_8$ groups;

$R_6$ is H, alkyl, haloalkyl, alcoxyalkyl, aryl, heterocyclyl, heteroaryl, cycloalkyl, benzyl, alkyl-aryl where $R_6$ is optionally substituted with one to four $R_8$ groups; and $R_8$: is halo, —$OR_{10}$, —$N(R_{10})_2$, —$SR_{10}$, —$SO_2R_{10}$, —$S(O_2)N(R_{10})_2$, —$S(O)_2OR_{10}$, —$N(R_{10})S(O)_2R_{10}$, —$OS(O)_2R_{10}$, —$C(O)R_{10}$, —$C(O)OR_{10}$, —C(O)N$(R_{10})_2$, —$OC(O)R_{10}$, —$OC(O)OR_{10}$, —OC(O)N$(R_{10})_2$, —$N(R_{10})C(O)R_{10}$, —$N(R_{10})C(O)OR_{10}$, —N$(R_{10})C(O)N(R_{10})_2$, —ON, —$NO_2$, alkyl, haloalkyl, alkyl-$OR_{10}$, or alkyl-$N(R_{10})_2$, where each $R_{10}$ is independently of H, alkyl, haloalkyl, cycloalkyl, heterocyclyl, aryl or heteroaryl; or

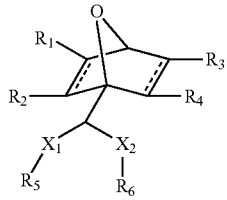
(ii)

and pharmaceutically acceptable solvates, salts and stereoisomers thereof, including mixtures thereof in all ratios, wherein:

wherein $R_1$, $R_2$, $R_3$ and $R_4$ are selected from the group consisting of H, and —C(O)—O—$R_7$;

wherein $X_1$ and $X_2$ are selected from the group consisting of C, N, O, S, and P;

wherein $R_5$ and $R_6$ are selected from the group consisting of alkyl, alkenyl, alkynyl, aryl, and heteroaryl; and wherein $R_7$ is alkyl.

2. The compound of claim 1, wherein the structure of the compound comprises

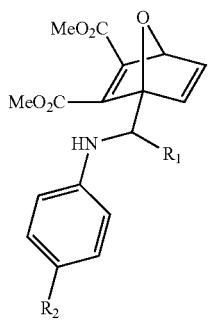

wherein $R_1$ is selected from $CH_2Ph$, $CH_2C_6H_4Me$, $CH_2C_6H_4OMe$, $CH_2C_6H_4F$, $CH_2C_6H_4OF_3$ n-Pr, Allyl, Vinyl or Me; and wherein $R_2$ is selected from H, Cl, Me or OMe.

3. The compound of claim 2, wherein the compound is selected from the group having the structure of:

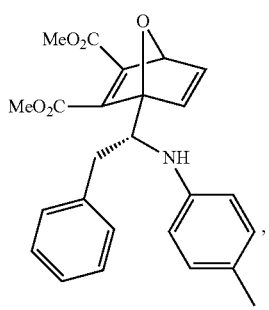

-continued

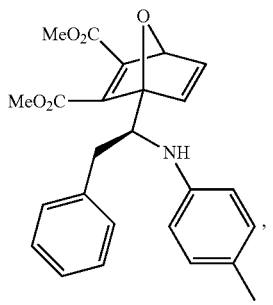

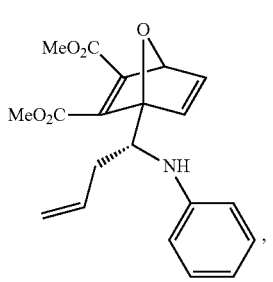

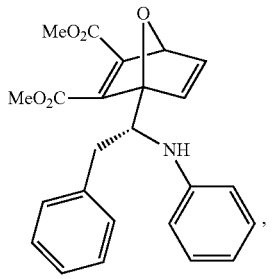

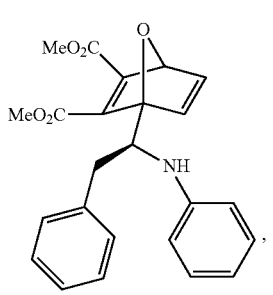

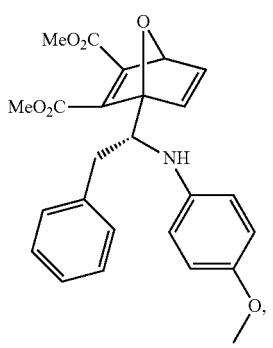

-continued
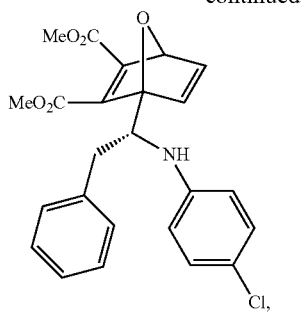
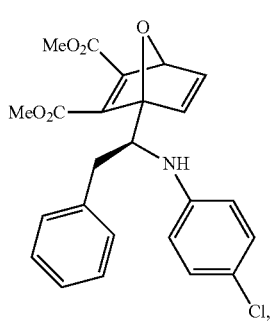
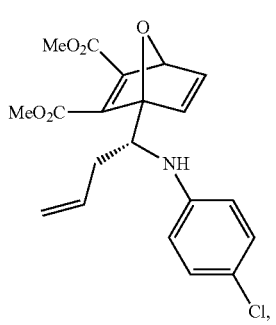
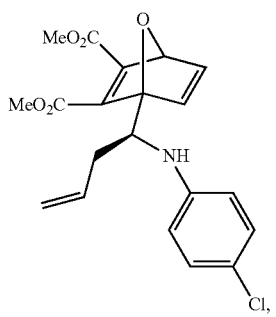
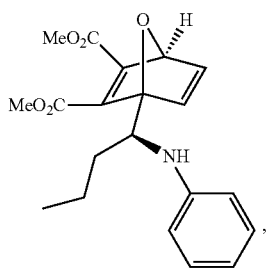
-continued
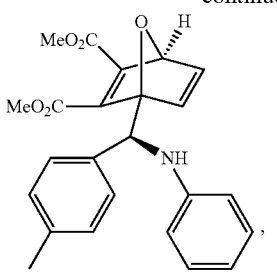
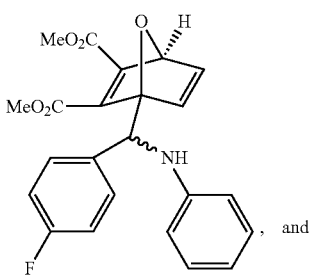
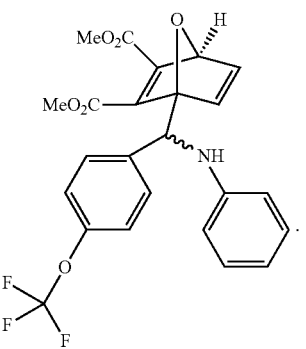
4. The compound of claim 2, wherein the compound is
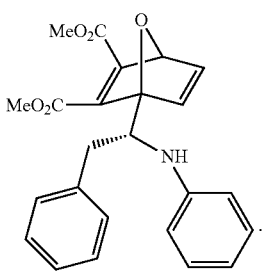
5. The compound of claim 2, wherein the compound is
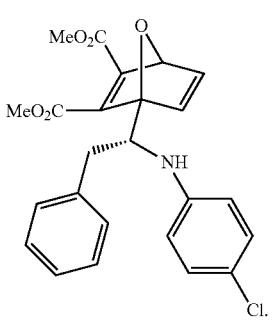 [SMILES: COC(=O)C1=C(C(=O)OC)C2([C@@H](Cc3ccccc3)Nc3ccc(Cl)cc3)C=CC1O2]

6. A method for inhibiting a SUMOylation enzyme in a cell, comprising administering an effective amount of a SUMOylation inhibitor compound to the cell, the compound comprising a structure:

(i)
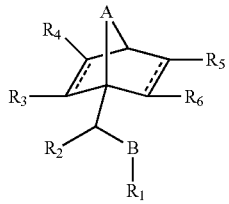

Or a pharmaceutically acceptable solvate, salt and stereoisomer thereof, including mixtures thereof in all ratios, wherein:
A is O, S, $NR_7$ where $R_7$ is H, alkyl, haloalkyl, alcoxyalkyl, aryl, heteroaryl, cycloalkyl, heterocyclyl, benzyl, alkyl-aryl where $R_7$ is optionally substituted with one to four $R_8$ groups, $CH_2$, $CH_2CH_2$, CH=CH;
B is O, S, $NR_{11}$ where $R_{11}$ is H, alkyl, haloalkyl, alcoxyalkyl, aryl, heteroaryl, cycloalkyl, heterocyclyl, benzyl, alkyl-aryl where $R_{11}$ is optionally substituted with one to four $R_8$ groups;
$R_1$ is H, alkyl, haloalkyl, alcoxyalkyl, aryl, heterocyclyl, heteroaryl, cycloalkyl, benzyl, alkyl-aryl where $R_1$ is optionally substituted with one to four $R_8$ groups;
$R_2$ is H, alkyl, haloalkyl, alcoxyalkyl, aryl, heterocyclyl, heteroaryl, cycloalkyl, benzyl, alkyl-aryl where $R_2$ is optionally substituted with one to four $R_8$ groups;
$R_3$ is —C(O)—$OR_9$, CN, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;
$R_4$ is —C(O)—$OR_9$, CN, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;
$R_5$ is H, alkyl, haloalkyl, alcoxyalkyl, aryl, heterocyclyl, heteroaryl, cycloalkyl, benzyl, alkyl-aryl where $R_5$ is optionally substituted with one to four $R_8$ groups;
$R_6$ is H, alkyl, haloalkyl, alcoxyalkyl, aryl, heterocyclyl, heteroaryl, cycloalkyl, benzyl, alkyl-aryl where $R_6$ is optionally substituted with one to four $R_8$ groups; and
$R_8$: is halo, —$OR_{10}$, —N$(R_{10})_2$, —$SR_{10}$, —$SO_2R_{10}$, —S$(O_2)$N$(R_{10})_2$, —S$(O)_2OR_{10}$, —N$(R_{10})$S$(O)_2R_{10}$, —OS$(O)_2R_{10}$, —C(O)$R_{10}$, —C(O)O$R_{10}$, —C(O)N$(R_{10})_2$, —OC(O)$R_{10}$, —OC(O)O$R_{10}$, —OC(O)N$(R_{10})_2$, —N$(R_{10})$C(O)$R_{10}$, —N$(R_{10})$C(O)O$R_{10}$, —N$(R_{10})$C(O)N$(R_{10})_2$, —CN, —$NO_2$, alkyl, haloalkyl, alkyl-$OR_{10}$, or alkyl-N$(R_{10})_2$,
where each $R_{10}$ is independently of H, alkyl, haloalkyl, cycloalkyl, heterocyclyl, aryl or heteroaryl; or (ii)
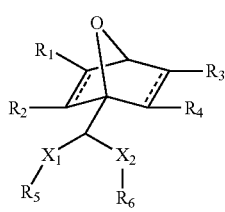

and pharmaceutically acceptable solvates, salts and stereoisomers thereof, including mixtures thereof in all ratios, wherein:

wherein $R_1$, $R_2$, $R_3$ and $R_4$ are selected from the group consisting of H, and —C(O)—O—$R_7$;
wherein $X_1$ and $X_2$ are selected from the group consisting of C, N, O, S, and P;
wherein $R_5$ and $R_6$ are selected from the group consisting of alkyl, alkenyl, alkynyl, aryl, and heteroaryl; and
wherein $R_7$ is alkyl.

7. The method of claim 6, wherein the structure of the compound comprises

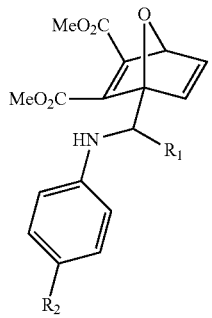

wherein $R_1$ is selected from $CH_2Ph$, $CH_2C_6H_4Me$, $CH_2C_6H_4OMe$, $CH_2C_6H_4F$, $CH_2C_6H_4OF_3$ n-Pr, Allyl, Vinyl or Me; and
wherein $R_2$ is selected from H, Cl, Me or OMe.

8. The method of claim 7, wherein the compound is selected from the group having the structure of:

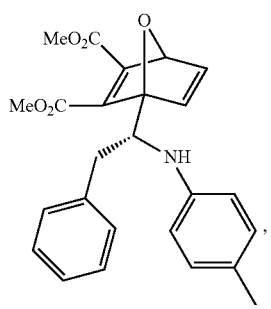

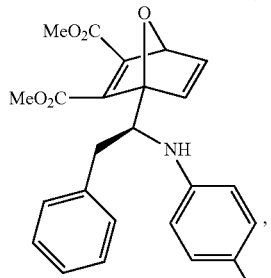

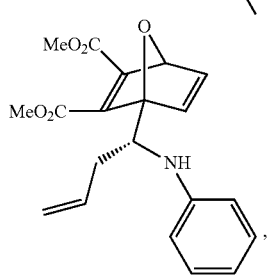

51
-continued
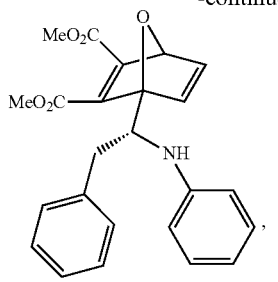
,
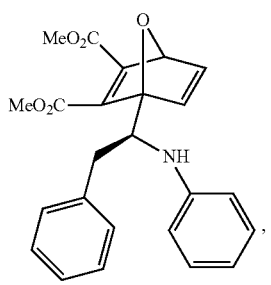
,
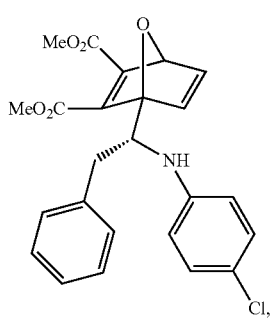
,
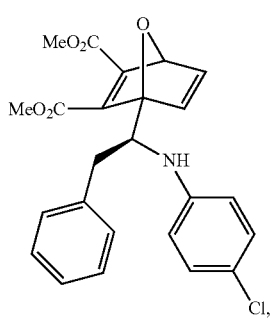
,
52
-continued
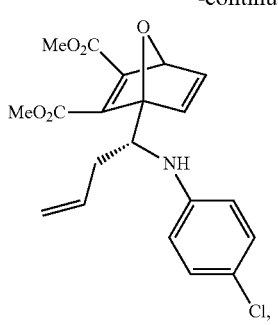
,
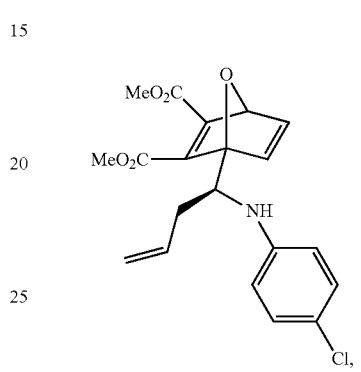
,
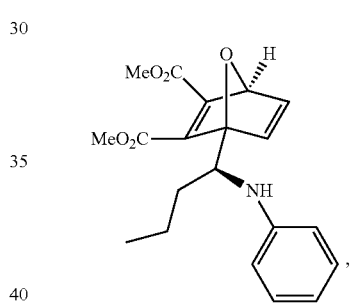
,
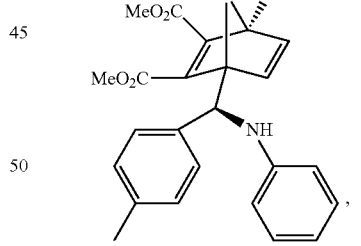
,
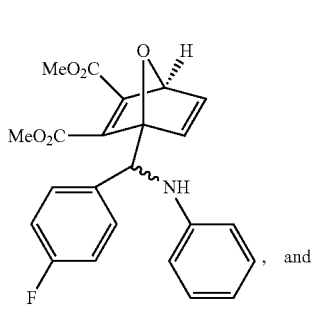
, and -continued

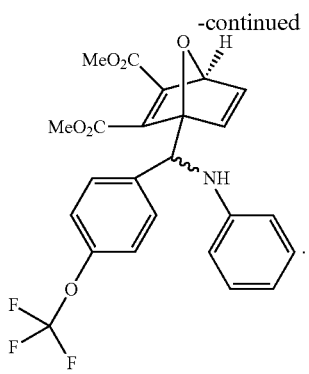

9. The method of claim 7, wherein the compound is

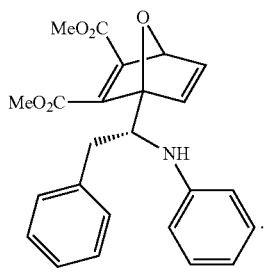 [SMILES: COC(=O)C1=C(C(=O)OC)C2([C@@H](Cc3ccccc3)Nc3ccccc3)C=CC1O2 ; "."]

10. The method of claim 7, wherein the compound is

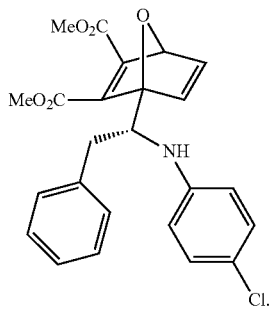 [SMILES: COC(=O)C1=C(C(=O)OC)C2([C@@H](Cc3ccccc3)Nc3ccc(Cl)cc3)C=CC1O2]

11. The method of claim 6, wherein the SUMOylation enzyme is SUMO E1 or SUMO E2.

12. The method of claim 6, wherein the cell is part of an in vivo population of cells in a subject.

13. The method of claim 12, wherein the population of cells is a tumor, a population of virally infected cells, a population of cells associated with heart disease, a population of cells associated with a degenerative disease, or a population of cells associated with a genetic disease.

14. The method of claim 6, wherein the cell is part of a population of cells grown in culture.

15. The method of claim 14, wherein the cell is part of a primary cell line, a secondary cell line or an immortal cell line.

16. The method of claim 15, wherein the cell line is derived from a tumor, a degenerative disease, a genetic disease or a cardiovascular disease.

17. A method for treating a disease comprising administering an effective amount of a pharmaceutical composition to a subject having the disease, the pharmaceutical composition comprising a compound comprising the structure:

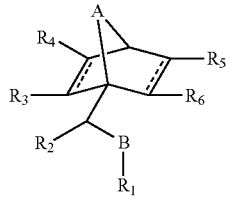
(i)

Or a pharmaceutically acceptable solvate, salt and stereoisomer thereof, including mixtures thereof in all ratios, wherein:

A is O, S, $NR_7$ where $R_7$ is H, alkyl, haloalkyl, alcoxyalkyl, aryl, heteroaryl, cycloalkyl, heterocyclyl, benzyl, alkyl-aryl where $R_7$ is optionally substituted with one to four $R_8$ groups, $CH_2$, $CH_2CH_2$, CH=CH;

B is O, S, $NR_{11}$ where $R_{11}$ is H, alkyl, haloalkyl, alcoxyalkyl, aryl, heteroaryl, cycloalkyl, heterocyclyl, benzyl, alkyl-aryl where $R_{11}$ is optionally substituted with one to four $R_8$ groups;

$R_1$ is H, alkyl, haloalkyl, alcoxyalkyl, aryl, heterocyclyl, heteroaryl, cycloalkyl, benzyl, alkyl-aryl where $R_1$ is optionally substituted with one to four $R_8$ groups;

$R_2$ is H, alkyl, haloalkyl, alcoxyalkyl, aryl, heterocyclyl, heteroaryl, cycloalkyl, benzyl, alkyl-aryl where $R_2$ is optionally substituted with one to four $R_8$ groups;

$R_3$ is —C(O)—$OR_9$, CN, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;

$R_4$ is —C(O)—$OR_9$, CN, —C(O)—$NHR_9$, —C(O)—N$(R_9)_2$, —$SO_2R_9$ and $R_9$ is H, alkyl, haloalkyl, aryl, heteroaryl where $R_9$ is optionally substituted with one to four $R_8$ groups;

$R_5$ is H, alkyl, haloalkyl, alcoxyalkyl, aryl, heterocyclyl, heteroaryl, cycloalkyl, benzyl, alkyl-aryl where $R_5$ is optionally substituted with one to four $R_8$ groups;

$R_6$ is H, alkyl, haloalkyl, alcoxyalkyl, aryl, heterocyclyl, heteroaryl, cycloalkyl, benzyl, alkyl-aryl where $R_6$ is optionally substituted with one to four $R_8$ groups; and $R_8$: is halo, —$OR_{10}$, —$N(R_{10})_2$, —$SR_{10}$, —$SO_2R_{10}$, —$S(O_2)N(R_{10})_2$, —$S(O)_2OR_{10}$, —$N(R_{10})S(O)_2R_{10}$, —$OS(O)_2R_{10}$, —$C(O)R_{10}$, —$C(O)OR_{10}$, —$C(O)N(R_{10})_2$, —$OC(O)R_{10}$, —$OC(O)OR_{10}$, —$OC(O)N(R_{10})_2$, —$N(R_{10})C(O)R_{10}$, —$N(R_{10})C(O)OR_{10}$, —$N(R_{10})C(O)N(R_{10})_2$, —CN, —$NO_2$, alkyl, haloalkyl, alkyl-$OR_{10}$, or alkyl-$N(R_{10})_2$, where each $R_{10}$ is independently of H, alkyl, haloalkyl, cycloalkyl, heterocyclyl, aryl or heteroaryl; or

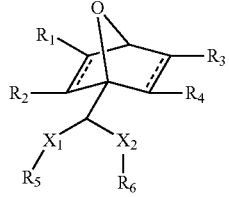
(ii)

and pharmaceutically acceptable solvates, salts and stereoisomers thereof, including mixtures thereof in all ratios, wherein:

wherein $R_1$, $R_2$, $R_3$ and $R_4$ are selected from the group consisting of H, and —C(O)—O—$R_7$;

wherein $X_1$ and $X_2$ are selected from the group consisting of C, N, O, S, and P;

wherein $R_5$ and $R_6$ are selected from the group consisting of alkyl, alkenyl, alkynyl, aryl, and heteroaryl;

wherein $R_7$ is alkyl; and wherein said disease is selected from colorectal cancer, pancreatic cancer, bone cancer or breast cancer.

18. The method of claim 17, wherein the structure of the compound comprises

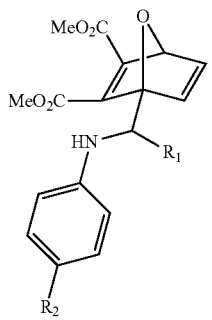

wherein $R_1$ is selected from $CH_2Ph$, $CH_2C_6H_4Me$, $CH_2C_6H_4OMe$, $CH_2C_6H_4F$, $CH_2C_6H_4OF_3$ n-Pr, Allyl, Vinyl or Me; and wherein $R_2$ is selected from H, Cl, Me or OMe.

19. The method of claim 18, wherein the compound is selected from the group having the structure of:

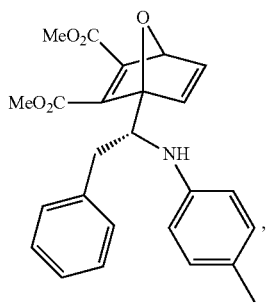

,

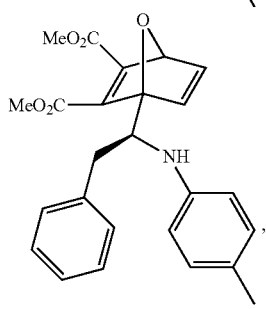

,

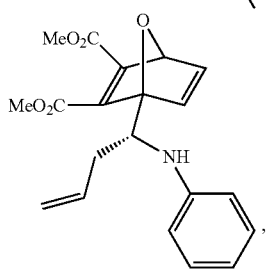

,

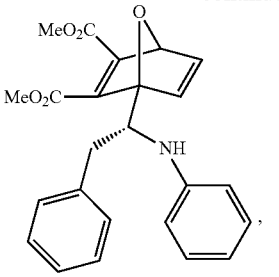

,

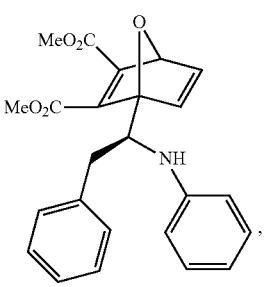

,

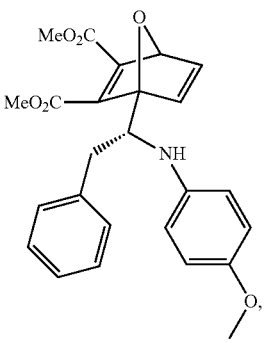

,

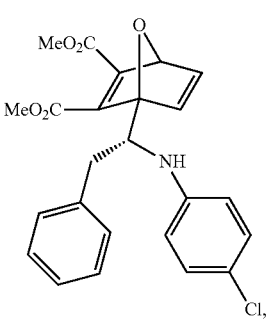

,

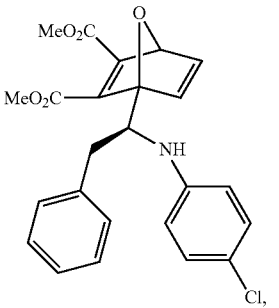

,

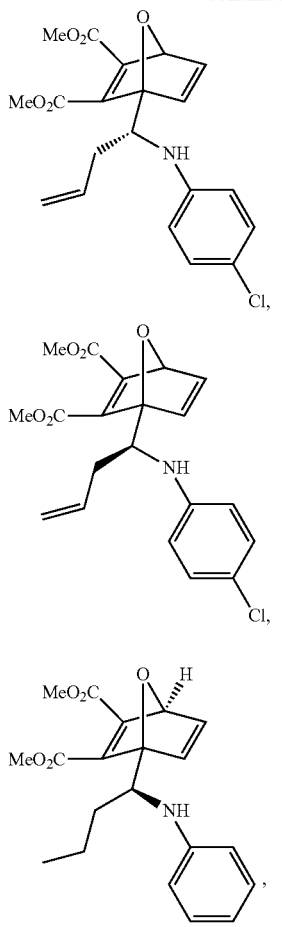
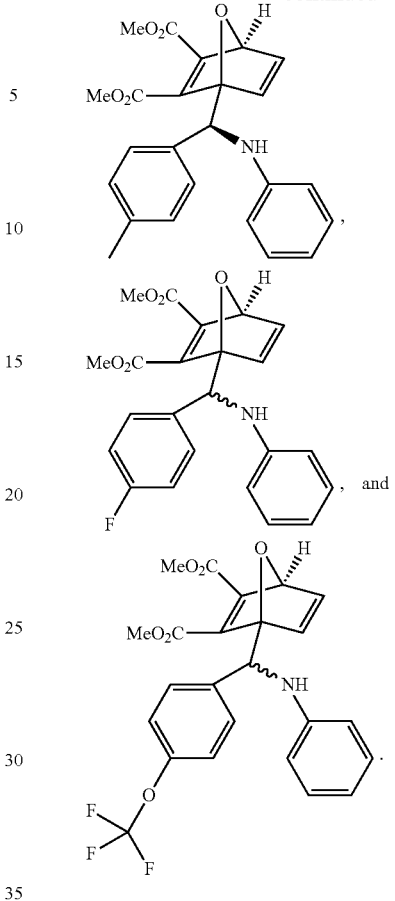
* * * * *